(12) United States Patent
Cesarek et al.

(10) Patent No.: US 10,233,419 B2
(45) Date of Patent: Mar. 19, 2019

(54) APPARATUSES AND METHODS FOR ELECTROPORATION

(71) Applicant: Zymergen Inc., Emeryville, CA (US)

(72) Inventors: John Cesarek, Redwood City, CA (US); Travis Lee, Burlingame, CA (US); Richard Hansen, San Carlos, CA (US)

(73) Assignee: Zymergen Inc., Emeryville, CA (US)

( * ) Notice: Subject to any disclaimer, the term of this patent is extended or adjusted under 35 U.S.C. 154(b) by 142 days.

(21) Appl. No.: 15/199,549

(22) Filed: Jun. 30, 2016

(65) Prior Publication Data

US 2018/0002652 A1    Jan. 4, 2018

(51) Int. Cl.
| C12M 1/42 | (2006.01) |
| C12M 1/02 | (2006.01) |
| C12M 1/24 | (2006.01) |
| B01L 3/14 | (2006.01) |
| B01L 7/02 | (2006.01) |
| C12N 15/87 | (2006.01) |

(52) U.S. Cl.
CPC ............. *C12M 35/02* (2013.01); *C12N 15/87* (2013.01)

(58) Field of Classification Search
CPC ................. C12M 35/02; C12N 15/87
USPC ........................................ 435/285.2
See application file for complete search history.

(56) References Cited

U.S. PATENT DOCUMENTS

| 2004/0130339 A1 | 7/2004 | Su et al. |
| 2005/0013745 A1* | 1/2005 | Buchanan ........... B01L 3/50855 422/400 |
| 2006/0087522 A1 | 4/2006 | Muller-Hartmann et al. |
| 2008/0029248 A1* | 2/2008 | Magnant ................... B01L 7/00 165/104.19 |

FOREIGN PATENT DOCUMENTS

WO    WO 2003/057819    7/2003

OTHER PUBLICATIONS

International Search Report and Written Opinion dated Sep. 13, 2017, for International Patent Application No. PCT/US17/040114.

\* cited by examiner

*Primary Examiner* — Sean E Conley
*Assistant Examiner* — Holly M Mull
(74) *Attorney, Agent, or Firm* — Weaver Austin Villeneuve & Sampson LLP

(57) ABSTRACT

Disclosed are apparatuses, systems, and methods for performing electroporation.

24 Claims, 14 Drawing Sheets

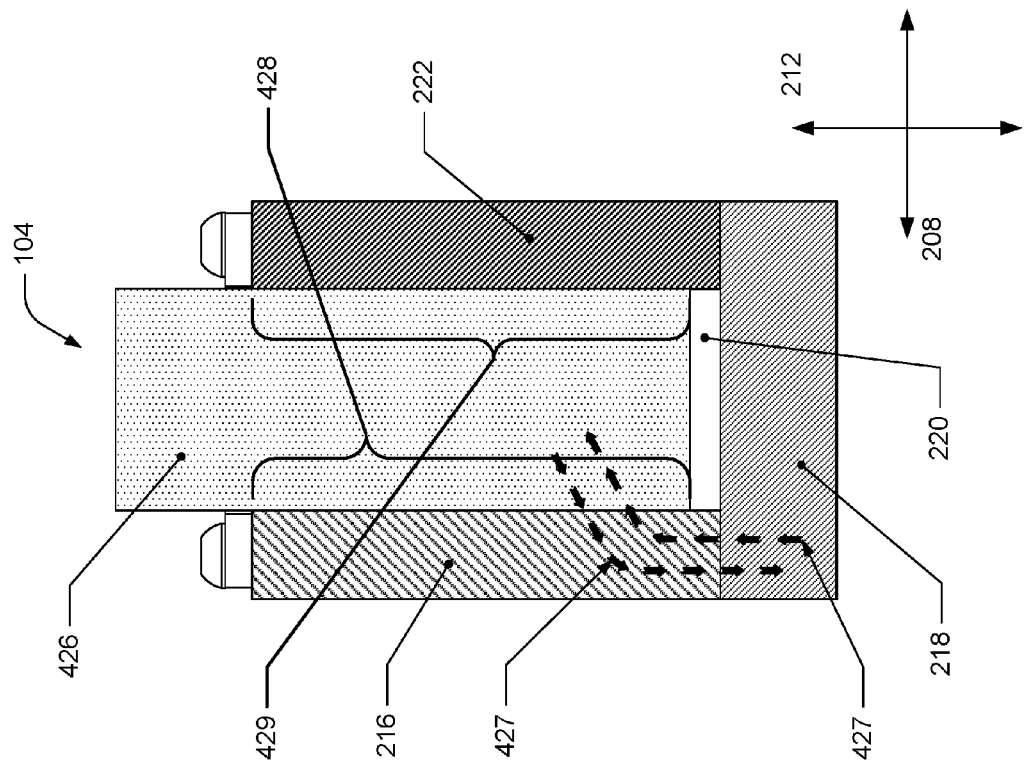
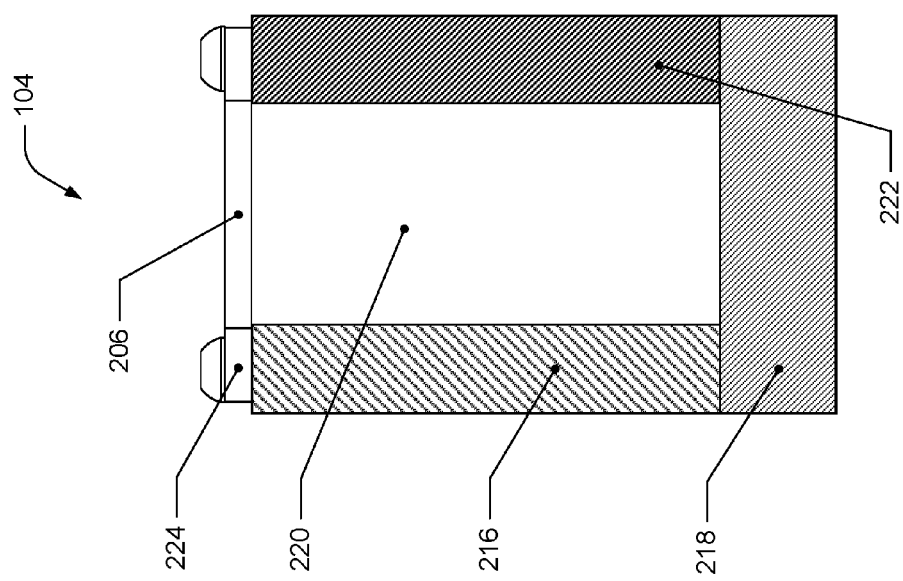
Figure 4
Figure 3

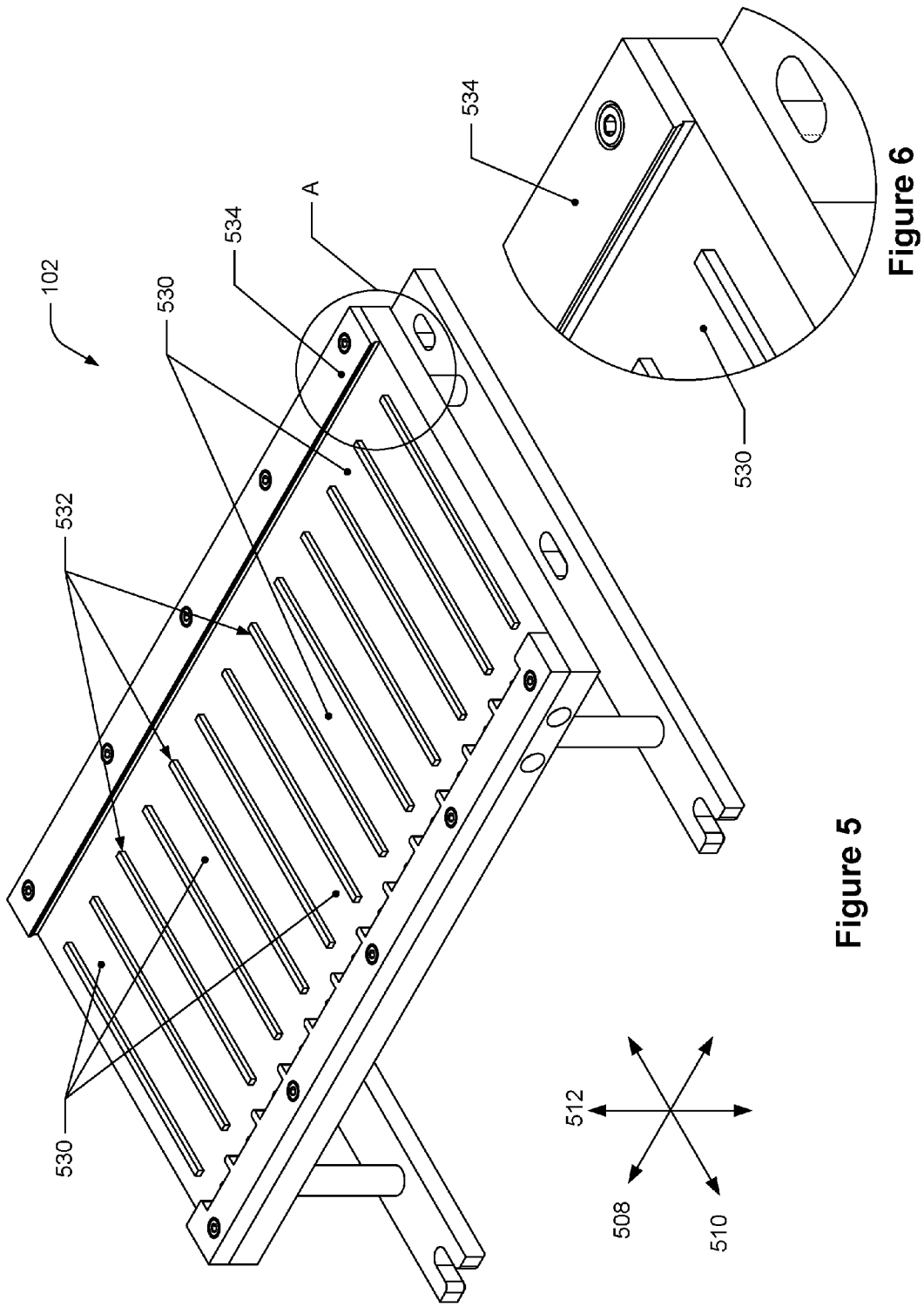

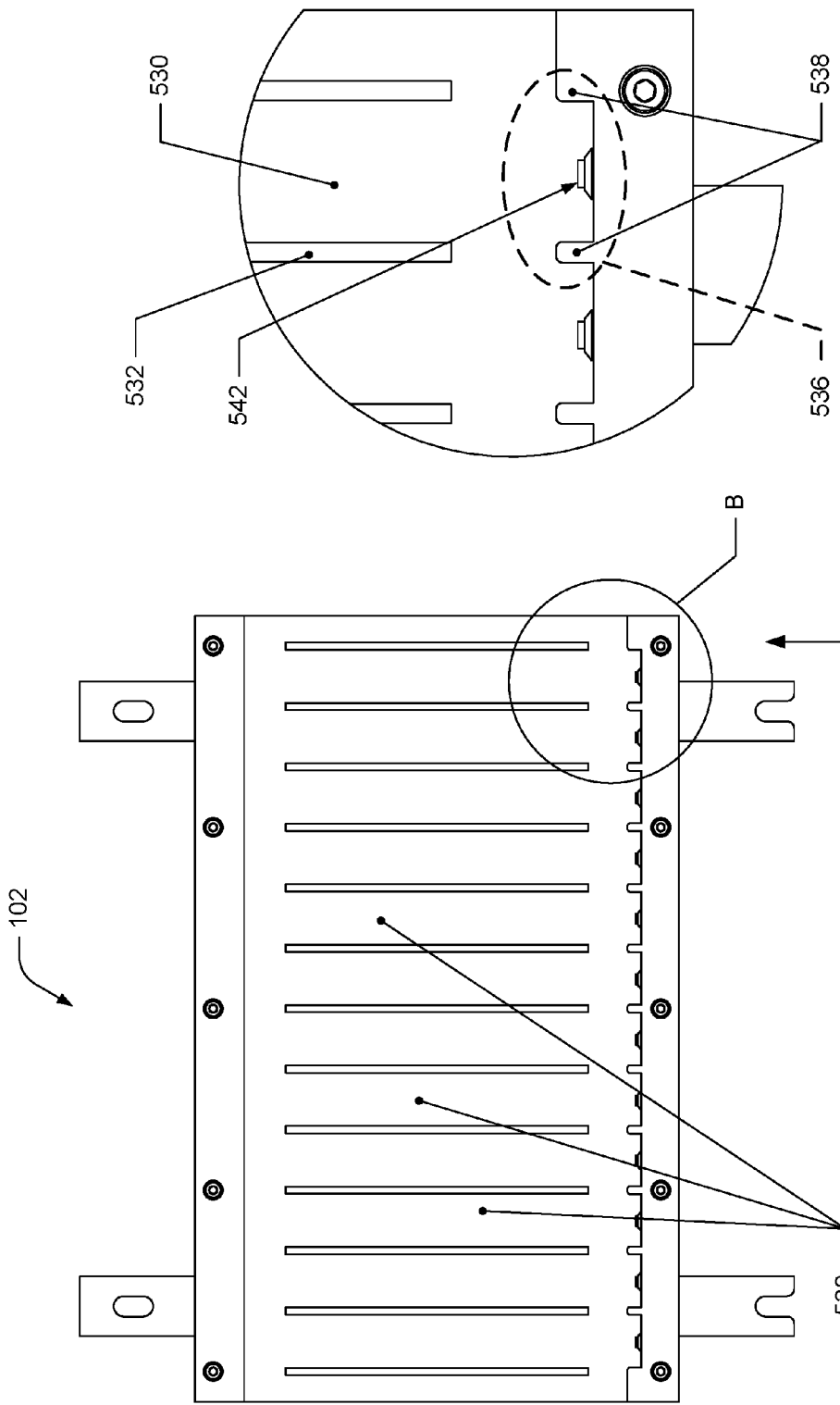

APPARATUSES AND METHODS FOR ELECTROPORATION

BACKGROUND

Electroporation is a method by which material can be introduced into cells. A solution containing cells and the material to be introduced are exposed to a brief high intensity electric field. The electric field porates the cells, producing transient pores in their outer membranes, allowing diffusion of the material in the solution into the cells. In one example, DNA plasmids can be introduced into microbial cells by electroporation to transform the microbial cells.

BRIEF DESCRIPTION OF THE DRAWINGS

FIG. 3 depicts a cross-sectional view of the cuvette holder of FIG. 2.

FIG. 4 depicts a cross-sectional view of a cuvette inserted into the cuvette holder of FIG. 3.

FIG. 5 depicts an isometric view of an example plate.

FIG. 6 depicts a detail view of portion A of the plate of FIG. 5.

FIG. 7 depicts a top view of the plate of FIG. 5.

FIG. 8 depicts a detail view of portion B of the plate of FIG. 7.

SUMMARY

Figure 1:
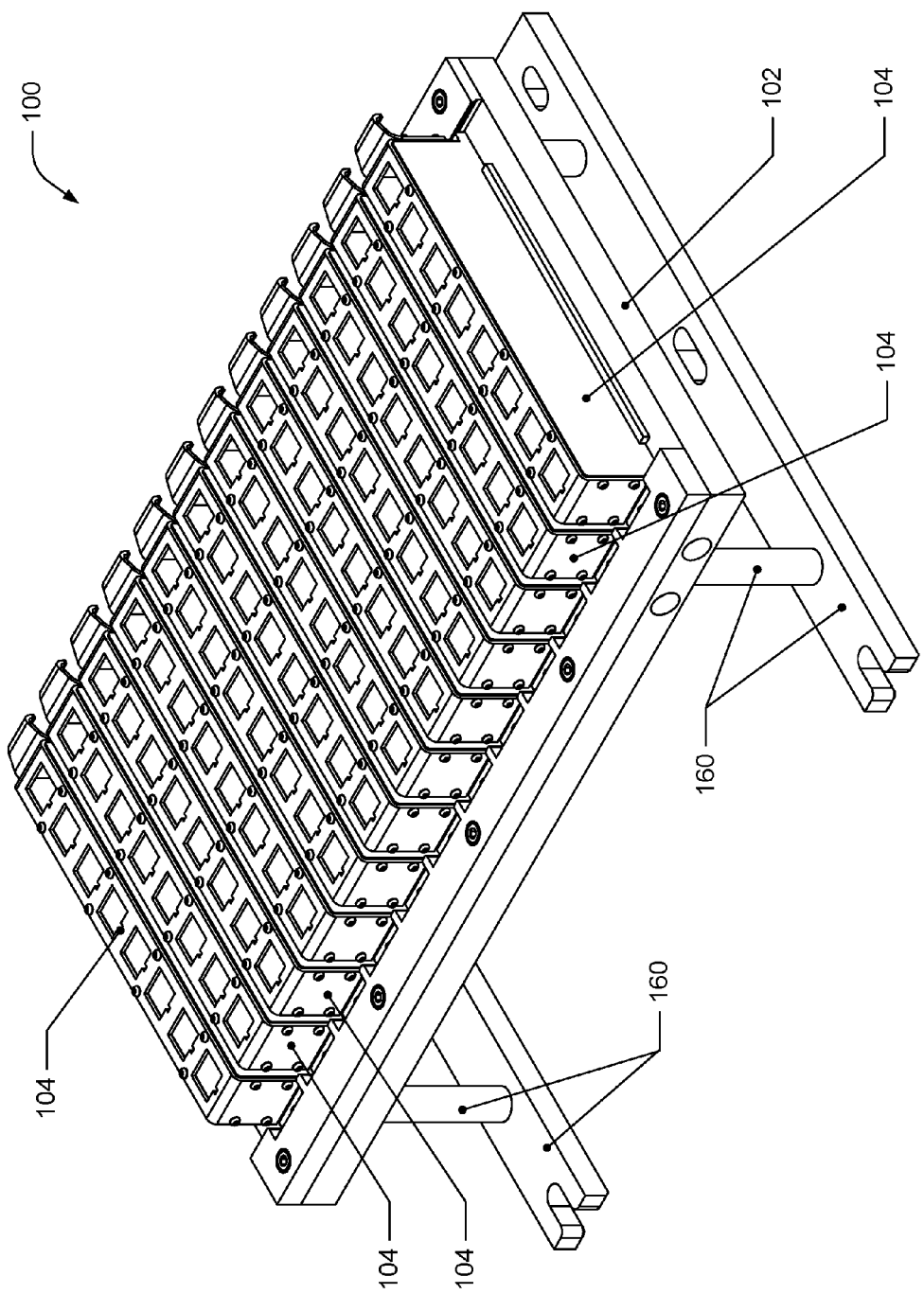
FIG. 1 depicts an isometric view of an example apparatus for holding and cooling a plurality of cuvettes.

In one embodiment, an apparatus may be provided. The apparatus may include a plurality of cuvette holders and each cuvette holder may be configured to hold a plurality of cuvettes, may include a bottom having a thermal conductivity greater than 150 W/(m K), a sidewall having a thermal conductivity greater than 150 W/(m K), and a plurality of cuvette positioning features. The sidewall and the bottom may be in thermal connection with each other and at least partially define an internal volume of the cuvette holder and each cuvette positioning feature may be configured to restrain a movement of a cuvette that is inserted into the internal volume such that a portion of each cuvette that is inserted into the internal volume is in thermal connection with the sidewall. The apparatus may also include a plate that may have a thermal conductivity greater than 150 W/(m K) and may include a first surface and a plurality alignment features. Each alignment feature may be configured to restrain a movement of a cuvette holder that is positioned on the first surface with respect to the first surface and the bottom of each cuvette holder that is placed on the first surface and restrained by at least one alignment feature is in thermal connection with the first surface. The apparatus may also include a fluid flowpath in thermal connection with the first surface.

In some embodiments, each cuvette holder may further include a second sidewall having a thermal conductivity greater than 150 W/(m K), the second sidewall may be in thermal connection with the bottom, and each cuvette positioning feature may be further configured to restrain a movement of a cuvette that is inserted into the internal volume such that a second portion of each cuvette that is inserted into the internal volume is in thermal connection with the second sidewall.

In some embodiments, each cuvette holder may include a mounting feature configured to interface with an alignment feature of the plurality of alignment features to restrain a movement of the cuvette holder.

In some embodiments, each cuvette holder may be configured to hold exactly eight cuvettes.

In some embodiments, the plate may be configured to accommodate twelve cuvette holders on the first surface.

In some embodiments, each cuvette positioning feature may be configured to restrain a movement of a cuvette that is inserted into the internal volume such that the portion of each cuvette that is inserted into the internal volume is in direct thermal contact with the sidewall.

In some embodiments, a surface of the fluid flowpath may be defined, at least in part, by the plate.

In some further embodiments, a surface of the fluid flowpath may be further defined, at least in part, by a cover over a second surface of the plate.

In some embodiments, the fluid flowpath may follow a serpentine path.

In some embodiments, the fluid flowpath may be configured to cause at least a section of the first surface on which the cuvette holders are disposed to have a substantially uniform temperature when a heat transfer fluid flows through the fluid flowpath.

In some further embodiments, a heat transfer fluid may flow through the fluid flowpath and may cause at least the section of the first surface to have a substantially uniform temperature.

In some embodiments, the apparatus may further include a pump and the pump may be configured to flow the heat transfer fluid through the fluid flowpath.

In some embodiments, the cuvette holder may be configured to hold N cuvettes and may further include a first electrode, and N second electrodes that are electrically isolated from each other and from the first electrode. Each cuvette positioning feature may be further configured to restrain a movement of a cuvette that is inserted into the internal volume such that a third portion of each cuvette that is inserted into the internal volume is electrically coupled to the first electrode, and a fourth portion of each cuvette that is inserted into the internal volume is electrically coupled to one corresponding Nth second electrode.

In some further embodiments, the sidewall may be electrically conductive and may be the first electrode.

In some other further embodiments, the apparatus may further include switching circuitry and each second electrode may be electrically coupled with the switching circuitry, and the switching circuitry may be configured to electrically couple one second electrode to a power supply while the other second electrodes are not electrically coupled to the power supply.

In some other further such embodiments, the apparatus may further include a controller that may be configured to control the switching circuitry and the controller may include control logic for causing the switching circuitry to alternatively electrically couple each second electrode to the power supply while the other second electrodes are not electrically coupled to the power supply.

In some other further such embodiments, the controller may further include control logic for measuring the resistance of a solution in a cuvette that has been inserted into the internal volume.

In some other further such embodiments, the controller may further include control logic for adjusting, based on the measurement of the resistance of the solution in the cuvette that has been inserted into the internal volume, one or more of the solution in that cuvette, the current to be applied to that cuvette, and the duration the current is to be applied to that cuvette.

In some other further embodiments, the apparatus may further include a plurality of cuvettes and each cuvette may be inserted in the internal volume of the cuvette holder, a movement of each cuvette may be restrained by a corresponding cuvette positioning feature, a third portion of each cuvette may be electrically coupled to the first electrode, and a fourth portion of each cuvette may be electrically coupled to one corresponding Nth electrode.

In some other further such embodiments, the third portion of each cuvette may be the portion of that cuvette and the fourth portion of each cuvette may be the second portion of that cuvette.

In some embodiments, the apparatus may further include a plurality of cuvettes and each cuvette may be inserted in the internal volume of the cuvette holder, a movement of each cuvette may be restrained by a corresponding cuvette positioning feature, and a portion of each cuvette may be in thermal connection with the sidewall.

In some embodiments, the apparatus may be configured to place 96 cuvettes in thermal connection with the first surface of the plate at one time.

In some embodiments, a method of electroporation may be provided. The method may include cooling a plurality of cuvettes containing a solution and inserted into a cuvette holder that is positioned on a first surface of a plate by flowing a heat transfer fluid through a fluid flow path that is in thermal connection to the first surface. A bottom of the cuvette holder may be in thermal connection with the first surface and with a sidewall of the cuvette holder, and the sidewall may be in thermal connection with a portion of each cuvette. The method may also include driving, after cooling the plurality of cuvettes to a first temperature, a current alternately to each cuvette. The current may flow through a second portion of a cuvette, through the solution of that cuvette, and through a portion of the cuvette to a ground.

In some embodiments, driving the current alternately to each cuvette may include driving the current alternately to a plurality of second electrodes on the cuvette holder, a second portion of each cuvette may be electrically coupled to one second electrode, the portion of each cuvette may be electrically coupled to a first electrode that is electrically coupled to the ground, and for each cuvette the current may flow from the corresponding second electrode through the second portion of that cuvette, through the solution of that cuvette, and through the portion of that cuvette to the ground.

In some embodiments, the method may further include measuring, before driving the current to one of the cuvettes, the resistance of the solution in that cuvette.

In some further embodiments, the method may further include adjusting, in response to the measurement and before driving the current to one of the cuvettes, one or more of the solution in that cuvette, the current to be applied to that cuvette, and the duration the current is to be applied to that cuvette.

In some embodiments, the method may further include positioning, after driving the current alternately to the plurality of cuvettes holder, the cuvette holder on a second surface of a second plate, and heating, after positioning the cuvette holder on the second surface of the second plate, the plurality of cuvettes inserted into the cuvette holder by flowing a heat transfer fluid through a second fluid flow path that is in thermal connection to the second surface. The bottom of the cuvette holder may be in thermal connection with the second surface and with the sidewall of the cuvette holder and the sidewall may be in thermal connection with the portion of each cuvette.

DETAILED DESCRIPTION

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific implementations, it will be understood that these implementations are not intended to be limiting. For example, while examples of the electroporation apparatuses given below are configured to hold 96 electroporation cuvettes for easy integration with 96-well plate liquid handling systems, it will be understood that the apparatuses may be configured to hold any number of cuvettes.

Disclosed herein are apparatuses, methods, and systems, for performing one or more aspects associated with electroporation. Electroporation (sometimes known as electropermeabilization) is a process in which an electrical field is applied across a solution containing cells. The electrical field causes increased permeability of the cell membrane of at least some of the cells in the solution. Some electroporation processes are used to introduce DNA, other chemicals, or other media into the cells. For example, electroporation of a solution containing bacterial cells and DNA may cause the cell membranes of the bacteria to increase in permeability, thus enabling the DNA to be introduced into the bacterial cells. Many electroporation processes drive a current across a relatively small distance, such as several millimeters, which creates an electric field across electrodes in close proximity that are held at large potentials and causes a current to run across the membranes of cells; the volume of solution that is electroporated varies, but may range, for instance, between about 50 microliters and about 400 microliters. As used herein, the term "electroporate" means to perform electroporation, i.e., to temporarily increase the permeability of cells by application of an electric field.

Electroporation processes may be performed using cuvettes that include two electrodes across which an electrical field may be applied. A cuvette is a container configured to hold a single sample of a particular volume. An electroporation cuvette is generally made of plastic, glass, or other electrically insulative material, with the electrodes made of an electrically conductive material, such as aluminum. Electroporation cuvettes are generally disposable. While electroporation may be performed in 96-well plates (some of which may have individual electrodes for each well), electroporation cuvettes provide various advantages. First, each sample in a cuvette is fluidically isolated from other samples in other cuvettes. Further, contamination or other failure of one well in a 96-well plate may require replacement of the entire plate, which has a much higher replacement cost than a single cuvette.

The apparatus and methods described herein may provide advantages over conventional methods of electroporation. In one conventional method, a user manually aspirates a volume of cells and a volume of DNA (or other material) into a cuvette for electroporation. Multiple cuvettes may be placed in an ice-bath to appropriately reduce the temperature, with samples manually added to the cuvettes. Such a technique is time-consuming, prone to error, and makes it difficult to maintain a uniform and constant temperature of the samples throughout the electroporation process. The use of liquid handling machines may enable faster throughput of aspirating the DNA and cells into a cuvette for electroporation. However, temperature control of the samples is difficult.

Electroporation may be performed according to a variety of process conditions including the voltage of the current applied to the solution, the duration for which the voltage is applied to the solution, the temperature of the solution (including, e.g., a uniform and consistent temperature of the solution throughout the electroporation process), the volume of the solution, and the resistance of the solution. For example, some electroporation processes are performed at temperatures ranging between about 2° C. and about 6° C., including at about 4° C. The particular process conditions may depend on the type of cells and material to be introduced therein. However, the apparatus and methods described herein are not limited to a particular set of process conditions.

Described herein are an apparatus and methods for performing high throughput and/or efficient electroporation. Some implementations involve controlling the temperature of cells and media for insertion into the cells. Temperature control of cuvettes, cells, or media to be inserted into the cells before, during, or after electroporation can be advantageous to the electroporation process by, among other things, increasing transfer efficiency. Transformation efficiency may be measured in transformants, e.g., a cell that has taken up a desired plasmid, or colony forming unit (cfu) per micro gram (µg) of DNA used. In some embodiments, temperature control may not directly result in efficiency of pore forming or update of DNA, but rather the ability of cells to survive the electroporation process. Accordingly, some embodiments of the present disclosure include an apparatus for holding and cooling a plurality of electroporation cuvettes. In some embodiments, the apparatus may be configured to maintain the cuvettes at a desired temperature for the duration of an electroporation process.

According to various embodiments, the electroporation may be performed when a cuvette is in or out of the apparatus. For example, an apparatus may hold 96 cuvettes and may cool the cuvettes to a desired temperature (e.g., about 4° C.). Once at the desired temperature, a user may remove one of the cuvettes from the apparatus and place the cuvette into a separate electroporation device that performs electroporation on the cuvette, after which the cuvette is returned to the apparatus. The user may then remove the next cuvette from the apparatus for electroporation, while all the other cuvettes in the apparatus remain at the desired temperature. This process may be repeated until all 96 cuvettes have been electroporated. Throughout the electroporation process, the cuvettes that have been electroporated and the cuvettes that will be electroporated are maintained by the apparatus at the desired temperature. In alternate embodiments, the apparatus may be configured such that electroporation is performed while the cuvettes are in the apparatus and are maintained at a desired temperature.

FIG. 1 depicts an isometric view of an example apparatus for holding and cooling a plurality of cuvettes. Apparatus 100 includes a plate 102 and a plurality of cuvette holders 104 that are configured to hold a plurality of cuvettes, disposed on the plate 102. In the example of FIG. 1, apparatus 100 includes twelve cuvette holders 104, each of which is configured to hold eight cuvettes. As discussed in greater detail below, the plate 102 and cuvette holders 104 are configured to interface with each other such that the cuvette holders are in thermal connection with the plate 102. The plate 102 is a heat sink (or in some embodiments, a heat source) such that cuvettes placed in a cuvette holder 104 that is disposed on the plate 102 can be maintained at a desired temperature. In some embodiments, a heat transfer fluid flowing through a flowpath in thermal connection with the plate 102 conducts heat between the plate 102, the plurality of cuvette holders 104, and a plurality of cuvettes that are inserted in the cuvette holders 104.

An Example Cuvette Holder

Figure 2:
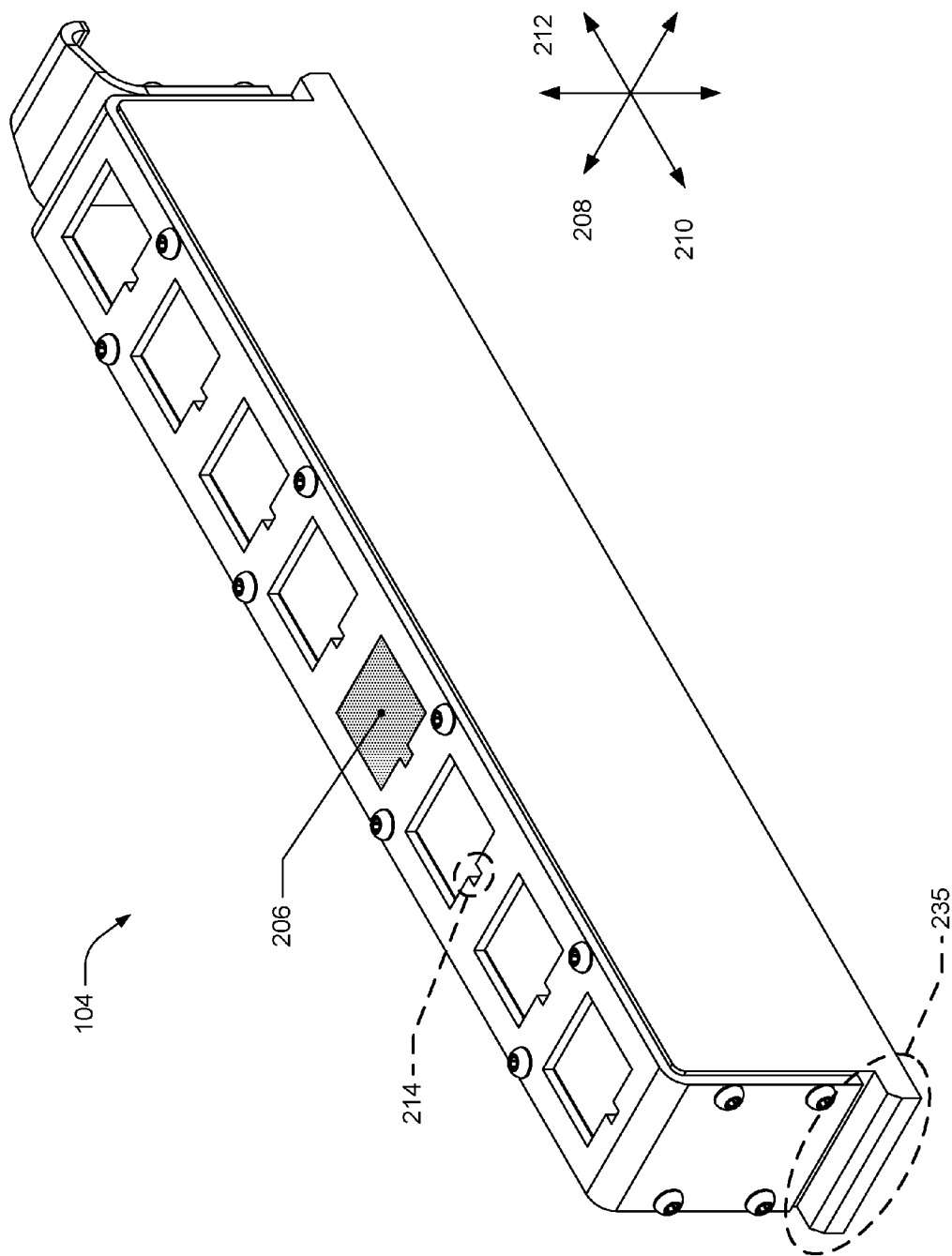
FIG. 2 depicts an isometric view of a cuvette holder of FIG. 1.

To enable thermal conduction to and from cuvettes inserted into a cuvette holder, the cuvette holder is configured such that there are thermal transfer pathways between the cuvette, the cuvette holder, and the plate. FIG. 2 depicts an isometric view of one of the cuvette holders of FIG. 1. It should be noted that cuvette holder 104 discussed herein is one example embodiment of a cuvette holder. Other example embodiments of cuvette holders that are configured to perform electroporation of cuvettes inserted into a second example cuvette holder are discussed below with respect to FIGS. 13 through 17. As can be seen in FIG. 2, cuvette holder 104 is configured to accommodate eight cuvettes. Cuvette holder 104 may include a plurality of cuvette positioning features that may be configured to orient or restrain a movement of a cuvette that is inserted into the cuvette holder 104. In the example of FIG. 2, the cuvette holder 104 includes eight cuvette positioning features that are openings 206 in the cuvette holder 104; one opening 206 is identified with shading. These openings 206 enable cuvettes to be inserted into an internal volume of the cuvette holder 104, i.e., inserted vertically into the cuvette holder along the z-axis 212, but substantially restrain movement of the cuvette in the directions indicated along an x-axis 208 and a y-axis 210. Additionally, the opening 206 prevents a cuvette from rotating about the z-axis 212.

The cuvette holder may also include another cuvette positioning feature such as a notch 214 identified within the dashed ellipse of FIG. 2. The notch 214 may restrain movement of a cuvette such that the cuvette may only be inserted into the cuvette holder 104 in one orientation. For instance, some cuvettes have a protrusion extending from the outside of only one sidewall of the cuvette. The opening 206 and the notch 214 of the cuvette holder may be sized and arranged such that the cuvette will fit only through the opening 206 if the notch 214 and the protrusion are aligned. Other cuvette positioning features may include any other feature that restrains a movement of a cuvette, such as vertical guides along a sidewall of the cuvette or protrusions extending from a top surface of the cuvette holder.

The cuvette holder 104 may also include a sidewall and a bottom. FIG. 3 depicts a cross-sectional view of the cuvette holder of FIG. 2. The sidewall 216 and the bottom 218 are identified with different types of cross-hatching. The sidewall 216 and the bottom 218 may have a thermal conductivity of a metal or metal alloy, which may be greater than 150 Watt per meter per Kelvin ("W/(m K)") such as about 205 W/(m K) for aluminum or about 385 W/(m K) for copper. The sidewall 216 and the bottom 218 may be the same material or different materials and such materials may have high thermal conductivities for increased abilities to transfer heat. As can be seen in FIG. 3, the sidewall 216 and the bottom 218 are in direct contact with each other and are therefore in thermal connection with each other. As used herein, thermal connection means that a thermal pathway exists between two items such that heat may flow between the two items even if the two items are not in direct physical contact. For instance, a layer of material, such as copper, may be interposed between and directly contacting both the sidewall 216 and the bottom 218 thus causing sidewall 216 and the bottom 218 not to be in physical contact, but to be in thermal connection with each other because heat may flow between the sidewall 216 and the bottom 218 through the layer of material. According to various embodiments, the overall thermal conductivity of a thermal pathway may be greater than 150 W/(m K).

The sidewall 216 and the bottom 218 also may at least partially define an internal volume 220 of the cuvette holder 104. In some embodiments, the internal volume 220 may also be defined by at least one of a second sidewall 222 of the cuvette holder 104 and a top 224 of the cuvette holder 104. The openings 206 may extend through the top 224. The second sidewall 222 may be configured similarly or identically to sidewall 216, including having a thermal conductivity greater than 150 W/(m K) and being in direct physical contact, or at least in thermal connection, with the bottom 218. FIG. 3 depicts the second sidewall 222 in both direct physical contact and thermal connection with the bottom 218.

The cuvette positioning features, such as opening 206 identified in FIG. 3, may also be configured to restrain a movement of a cuvette that is inserted into the internal volume such that a portion of each cuvette that is inserted into the internal volume is in thermal connection with the sidewall. For example, as discussed above, opening 206 and/or the notch 214 may be configured (e.g., sized, spaced, and arranged on the cuvette holder 104) such that a movement of a cuvette inserted into the internal volume 220 is restrained to cause a portion of that cuvette to be in thermal contact with the sidewall 216.

FIG. 4 depicts a cross-sectional view of a cuvette inserted into the cuvette holder of FIG. 3. Cuvette 426 can be seen inserted into the internal volume 220 of the cuvette holder 104. The opening 206 restrains movement of the cuvette 426 to cause a portion 428 of the cuvette 426 to be in thermal connection with sidewall 216. For instance, movement of the cuvette 426 along the x-axis 208 is restrained. The portion 428 of the cuvette 426 is also in direct physical contact, and therefore direct thermal contact, with sidewall 216. At least some of the cuvette 426 may be made of a thermally conductive material. For example, the above-described electrodes of the cuvette 426 are typically thermally conductive. The portion 428 of the cuvette 426 may be made of multiple different materials, such as a metal of the electrode and a plastic, both of which may be in direct and thermal contact with the sidewall 216, but higher thermal conductivity may exist between a metal electrode of the cuvette 426 and the sidewall 216. The thermal connections between the cuvette, sidewall, and bottom create a thermal conduction pathway between all of these elements. Two exemplary thermal flows between the cuvette 426, sidewall 216, and bottom 218 are identified with arrows as feature 427.

In some embodiments, one or more layers of material may be interposed between the sidewall 216 and the portion 428 of the cuvette 426 but a thermal connection may still exist between the sidewall 216 and the portion 428 of the cuvette 426. In some embodiments, a bottom of the cuvette 426 (not identified) may be in thermal contact with the bottom 218 of the cuvette holder 104.

Although identified as separate elements, the cuvette holder may be constructed using traditional manufacturing techniques in which the bottom and sidewalls are separate elements that are joined or fastened together (e.g., by welding or with nuts and bolts) or the bottom and one or more sidewalls may be a single, continuous element which may be produced, for instance, by additive manufacturing (e.g., 3D printing).

The one or more cuvette positioning features, e.g., the opening 206 and/or the notch 214, of cuvette holder 104 may also restrain the movement of the cuvette 426 to cause a second portion 429 of the cuvette 426 to be in thermal connection, in direct physical contact, and/or in direct thermal contact with the second sidewall 222 as can be seen in FIG. 4. The second portion 429 of the cuvette 426 may be similar or identical to the portion 128 as described above, including, for instance, having at least some material that is thermally conductive, such as an electrode.

An Example Plate

As noted above, the apparatus 100 in FIG. 1 includes plate 102 on which the plurality of cuvette holders 104 may be disposed. In some embodiments, the plate 102 may be configured to receive and hold the plurality of cuvette holders and to create a thermal connection between the cuvette holder and the plate. FIG. 5 depicts an isometric view of an example plate. As can be seen, plate 102 includes a first surface 530 which is the surface on which the cuvette holders (not depicted) may be disposed. The plate 102, including the first surface 530, may be a material that has a thermal conductivity greater than 150 W/(m K) such as about 205 W/(m K) for aluminum or about 385 W/(m K) for copper. The plate and other aspects of the apparatus may also be constructed as described herein, such as by using traditional manufacturing techniques which may include additive manufacturing.

The plate 102 may also include a plurality of alignment features that are configured to constrain a movement of a cuvette holder that may be positioned on the first surface 530. As discussed in greater detail below, the alignment features may be configured to restrain the cuvette holders to a particular location, and in some cases in a particular orientation, that aligns and/or orients cuvettes inserted into the cuvette holders with one or more pipettes of a liquid handling machine. These alignment features may include grooves, protrusions, notches, pegs, clips, or other such features known in the art. For instance, FIG. 5 depicts a plurality of plateaus 532 disposed along the first surface 530 that extend away from the first surface 530 and that are configured to substantially restrain movement of a cuvette holder in the x-axis 508. Such configuration may allow for some movement in the x-axis 508 to allow placement and removal of the cuvette holder onto the plate 102, but not enough movement to allow the cuvette holder to move out of the desired alignment.

Another example alignment feature is a front guide 534 depicted in FIGS. 5 and 6; FIG. 6 depicts a detail view of portion A of the plate of FIG. 5. As can be seen, one part of the front guide 534 extends away from the first surface 530 in the z-axis 512 and another portion of the front guide 534 extends over the first surface 530 such that a recess is created that is configured to interface with a mounting feature on the cuvette holder, such as to receive the insertion of mounting feature 235 which is depicted in FIG. 2 as a protrusion of the cuvette holder 104. The cuvette holder may have a variety of mounting features known in the art that are configured to interface with at least one alignment feature of the plurality of alignment features in order to restrain a movement of the cuvette holder. The front guide 534 may thus restrain movement of the cuvette holder in at least one direction of the y-axis 510 and/or in at least one direction of the z-axis 512.

Other alignment features can be seen in FIGS. 7 and 8. FIG. 7 depicts a top view of the plate of FIG. 5 and FIG. 8 depicts a detail view of portion B of the plate of FIG. 7. The plate 102 and first surface 530 are identified in FIG. 7 and a rear guide 536 is identified within the dashed ellipse in FIG. 8. The rear guide 536 include protrusions 538 that extend in the y-axis 510 and are configured, similar to the plateaus, to restrain movement of the cuvette holder (not shown) in the x-axis 508.

In some embodiments, the alignment features, such as those described herein, may be configured to allow the cuvette holder to be removably restrained on the plate so that a user may place the cuvette holder on the plate and remove the cuvette holder from the plate. Such removable restraint enables the cuvette holder to be positioned onto the first plate and have some movement in the x-, y-, and/or z-axes restrained by the cuvette holder such that the cuvette holder is properly aligned, but such restraint is not permanent in that the cuvette holder may be removed from the plate after it is restrained by the alignment features. One such alignment feature may be a ball plunger 542 that is depicted in FIG. 8 and which may be configured to apply pressure onto the cuvette holder in the y-axis 510 as well as to restrain movement of the cuvette in the z-axis (not identified) while enabling the cuvette holder to be removably restrained on the first plate.

Other examples of alignment features enabling such removable restraint include clips and nuts and bolts. Moreover, even though these alignment features are depicted on plate 102, in some embodiments only some such features may be used while in other embodiments other alignment features may be used, such as pegs.

Referring back to FIGS. 1 and 5, plate 102 may be configured to accommodate a plurality of cuvette holders, such as twelve like depicted in these Figures. Such configuration of the plate 102 may include, for example, having a first surface 530 with a surface area large enough to accommodate all such cuvette holders simultaneously as well as having alignment features configured to restrain movement of the plurality of cuvette holders.

Figure 9:
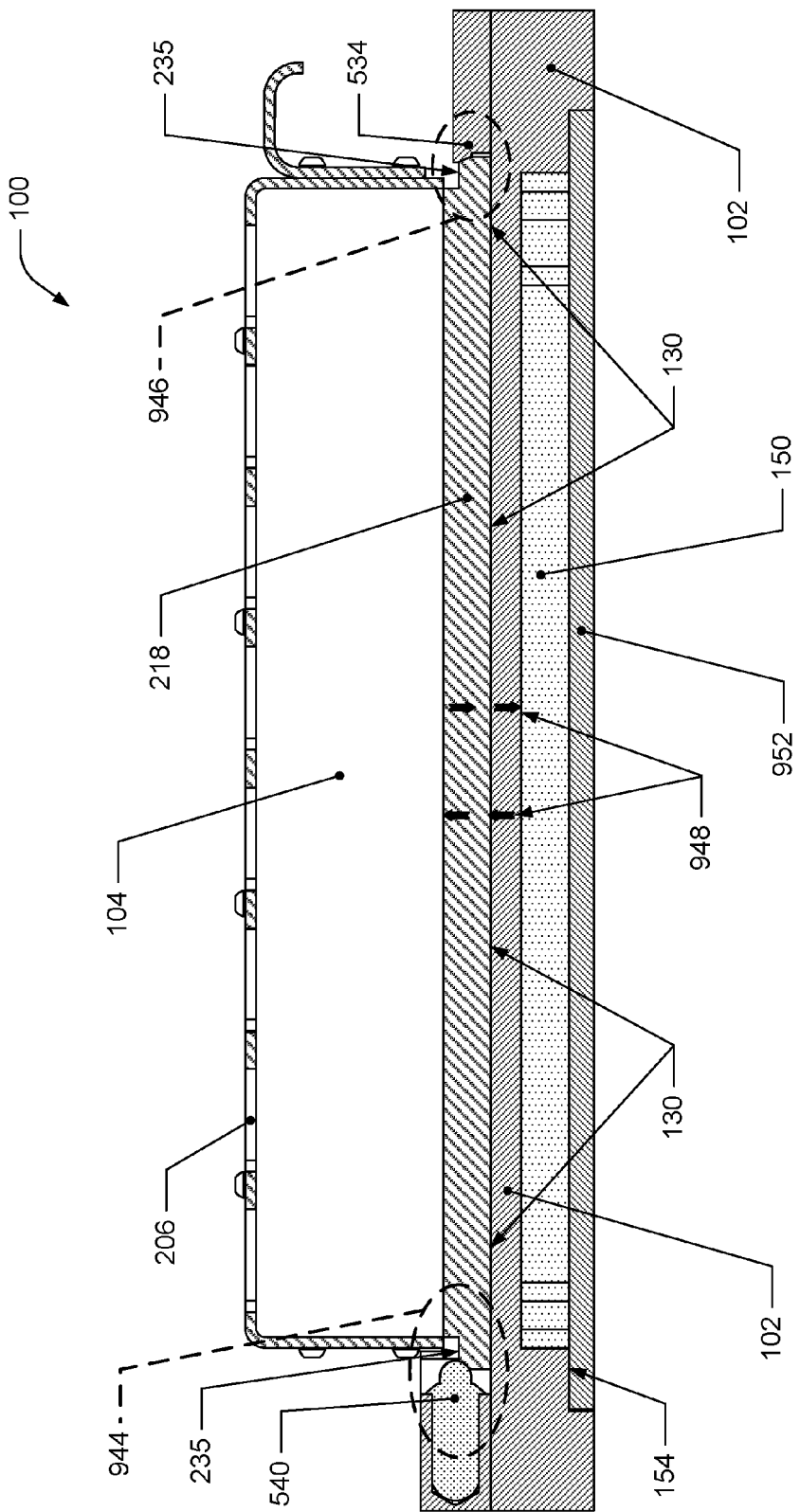
FIG. 9 depicts a cross-sectional side view of part of the apparatus.

Additionally, when a cuvette holder is placed on the first surface and restrained by at least one alignment feature, the bottom of that cuvette holder may be in thermal connection with the first surface. FIG. 9 depicts a cross-sectional side view of part of apparatus 100. One cuvette holder 104 can be seen along with the bottom 218 and one identified opening 206, i.e., one positioning feature. An example interface between a mounting feature of the cuvette holder and the alignment feature of the plate may be seen in a first interface 944 (identified with a dashed ellipse) between mounting feature 235 of cuvette holder 104 (e.g., a protrusion) and an alignment feature 540 of the plate (e.g., a ball plunger). Another example interface may be seen in a second interface 946 (identified with a dashed ellipse) between another mounting feature 235 of cuvette holder 104 (e.g., another protrusion) and the front guide 534 of the plate 102. The cuvette holder 104 can also be seen in direct physical contact, and therefore in direct thermal connection, with the first surface 130 of the plate 102; an exemplary thermal flow between these features is identified with arrows 948.

Figure 10:
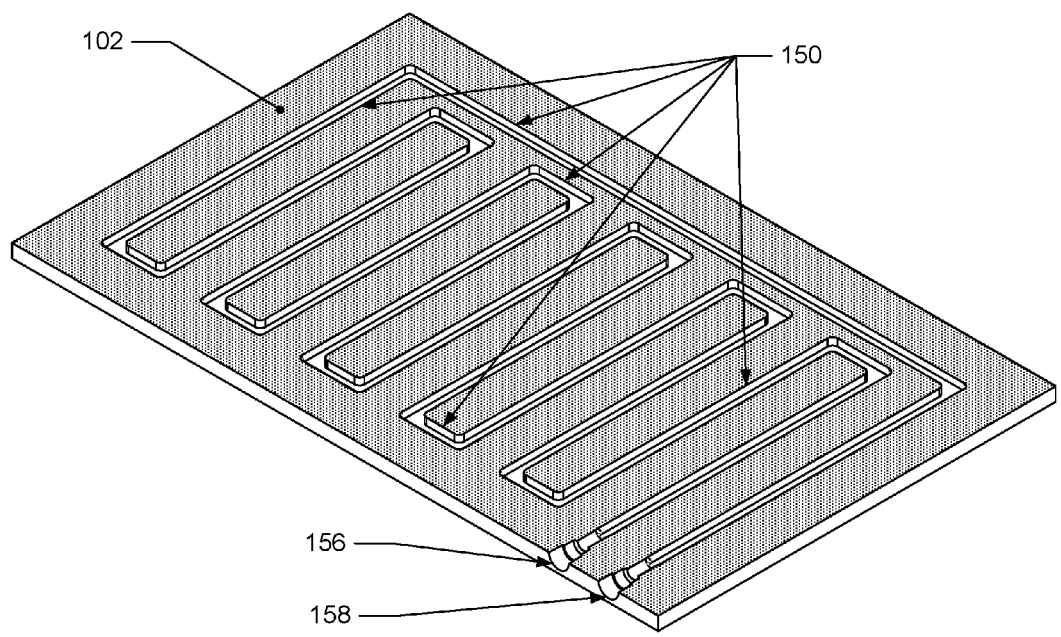
FIG. 10 depicts an isometric cross-sectional view of the plate.
Figure 11:
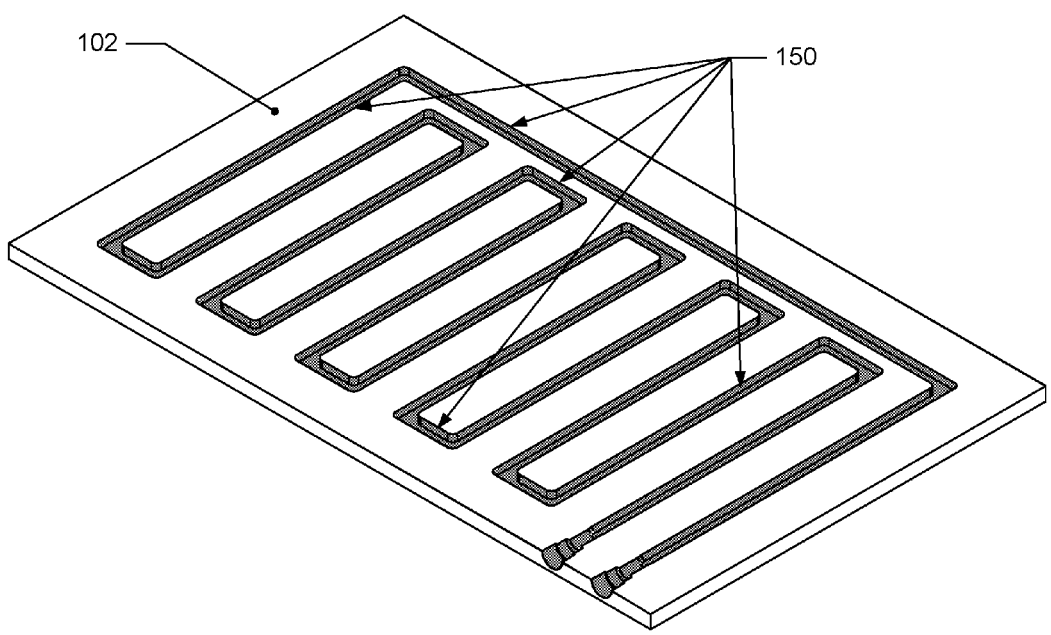
FIG. 11 depicts the isometric cross-sectional view of the plate of FIG. 10 with different shading.

The apparatus may also include a fluid flowpath that is in thermal connection with the first surface of the plate. This fluid flowpath may carry the heat transfer fluid which enables, for instance, the cooling of the cuvettes in the cuvette holders that are disposed on the first surface of the plate. FIG. 10 depicts an isometric cross-sectional view of the plate and FIG. 11 depicts the isometric cross-sectional view of the plate of FIG. 10 with different shading. For illustrative purposes, in FIG. 10 the sectioned surface of the plate 102 is shaded and a fluid flowpath 150 is unshaded, while in FIG. 11 the sectioned surface of the plate 102 is unshaded and the fluid flowpath 150 is shaded.

The fluid flowpath 150 may be arranged in a variety of different configurations in order to establish a thermal connection with and/or a uniform temperature of the first surface of the plate, such as a serpentine, corkscrew, and/or another arrangement that has linear and/or curved sections, such as curved corners. The fluid flowpath 150 may also include an inlet 156 and an outlet 158, as shown in FIG. 10, to enable the heat transfer fluid to flow through the entirety of the fluid flowpath 150. The majority of the fluid flowpath 150 depicted in FIGS. 10 and 11 follows a serpentine path. The configuration of the fluid flowpath 150 may also cause at least a section of the first surface 130 on which the cuvette holders are disposed to have a substantially uniform temperature (e.g., within +/−0.5° C.) when a heat transfer fluid flows through the fluid flowpath 150. The temperatures to which the plate, including the first surface, may be set vary upon the numerous factors, including the electroporation process to be performed and the liquids and media used in such electroporation. For instance, the plate may be set to a temperature between about 2° C. and about 4° C., or between about −15° C. and about 65° C., or to any other temperature that may be desired for a particular electroporation process. Such a configuration may thereby cause the cuvettes inserted into the cuvette holders to have a substantially uniform temperature. Referring back to FIG. 9, the exemplary thermal flow identified with arrows 948 may also depict the thermal transfer path between the fluid flowpath 150, the plate 102, the first surface 130, and the bottom 218 of the cuvette holder 104.

The apparatus set forth herein may be used to cause the plate to have a uniform temperature of a wide range of temperatures which may cool and/or heat cuvettes in cuvette holders disposed on the plate. For example, the fluid flowpath may flow a heat transfer fluid that may cool the cuvettes to a variety of temperatures, such as about −30° C. to about 30° C. Or, for instance, the fluid flowpath may flow a heat transfer fluid that may heat the cuvettes to a variety of temperatures, such as about 35° C. to about 70° C. In some embodiments, a plurality of heat transfer fluids at different temperatures may be fluidically connected to a single fluid flowpath and the apparatus may be configured (e.g., containing valves, tubing, or the like) to flow the plurality of heat transfer fluids through the same fluid flowpath at different times.

In some embodiments, the plate may be configured to heat cuvettes in cuvette holders disposed on the plate through the use of a heating element and in some such embodiments, the apparatus may therefore not include a fluid flowpath. The heating element may be any known heater, such as a resistive heater embedded in a ceramic.

In some embodiments, a surface of the fluid flowpath 150 may be defined in whole or in part by the plate 150, while in some other embodiments the fluid flowpath may be separate from the plate (e.g., a pipe or tube attached to the plate 102). For instance, the fluid flowpath 150 may be fully defined by the plate 102 such that the fluid flowpath 150 is within a body of the plate 150. In other embodiments, such as that depicted in FIG. 9, a surface of fluid flowpath 150 may be partially defined by the plate 102 while another surface of the fluid flowpath 150 may be defined by a cover 952 that is placed over a second surface 154 of the plate 102. In some such embodiments, the majority of the fluid flowpath, such as the curved, e.g., tubular, portion of the cross-sectional area and its pathway through the plate, may be defined by the plate while the cover simply covers and fluidically seals the fluid flowpath.

Other Apparatus Features

Figure 12:
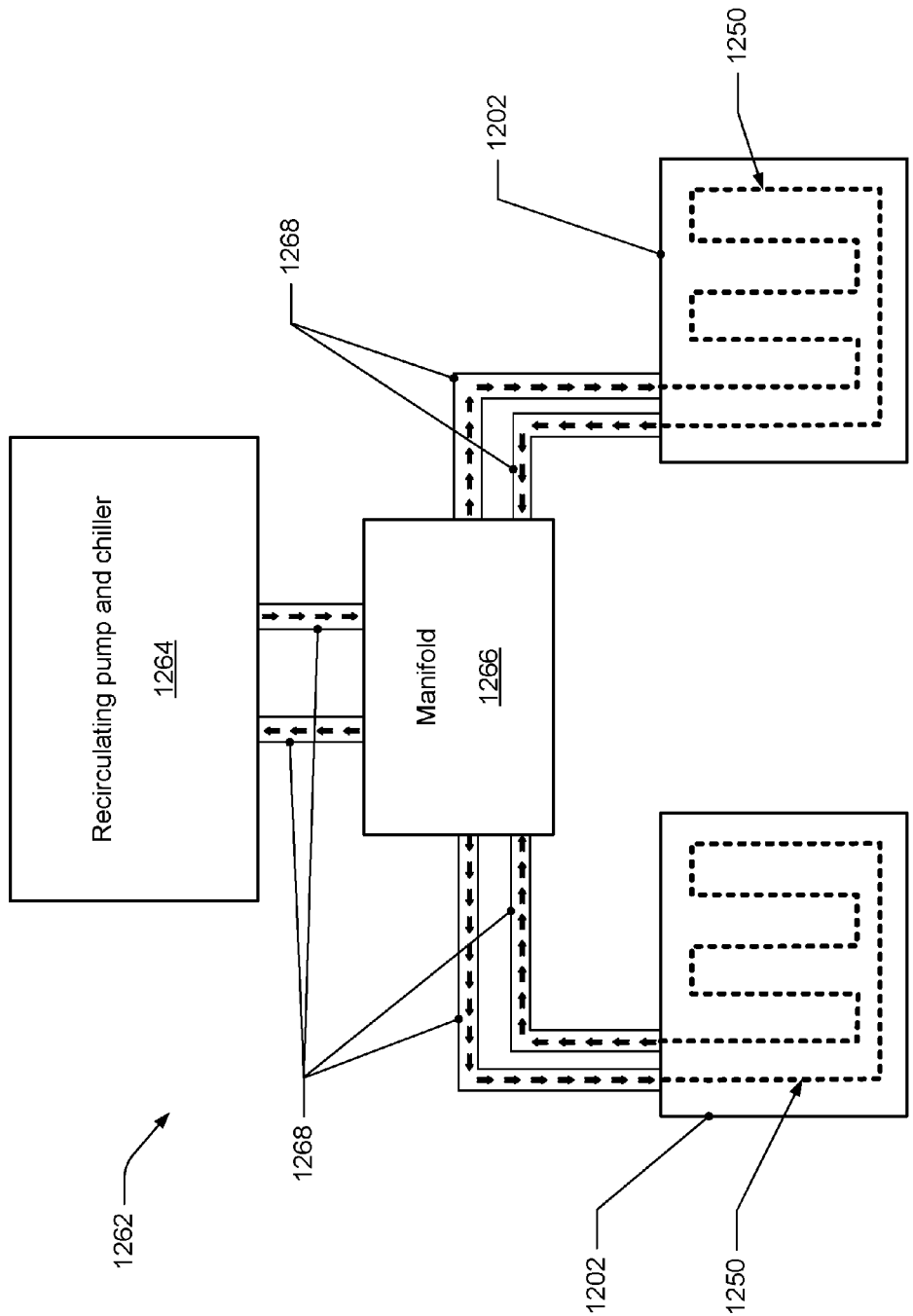
FIG. 12 depicts an example system.

In some embodiments, the apparatus may contain a pump, e.g., a cooling recirculator, that is configured to flow the heat transfer fluid through the fluid flowpath. The apparatus may also include a manifold that is fluidically connected to the pump and to a plurality of fluid flowpaths, with each fluid flowpath thermally connected to one of a plurality of plates. Such configuration may also be considered a system which may include the same elements. For instance, FIG. 12 depicts an example system 1262 that includes a recirculating pump and chiller 1264 fluidically connected with a manifold 1266 through the uses of pipes 1268 (which may be tubes or other flow passages), two fluid flowpaths 1250 fluidically connected to the manifold through the use of pipes 1268 and in thermal connection with the first surfaces of each of the two plates 1202. System 1262 may be configured to recirculate chilled flow from the recirculating pump and chiller 1264 to the manifold 1266, from the manifold 1266 to each fluid flowpath 1250, and from the fluid flowpath 1250 back to the recirculating pump and chiller 1264.

In some embodiments, the apparatus may be configured to be positioned inside a liquid handling machine to enable some automated liquid handling of the liquids and elements associated with electroporation (e.g., cells or media to be inserted into the cells) while the cuvettes holding such liquids or elements and positioned in cuvette holders disposed on the plate are cooled or heated. This configuration may include, for instance, configuring each cuvette holder to hold a number of cuvettes that matches the number of pipette tips of the liquid handling machine, configuring the positioning features of the cuvette holder such that the cuvettes in the cuvette holder align with the pipette tips of the liquid handling machine, and/or configuring the alignment features of the plate to align the cuvette holders such that the cuvettes in the cuvette holders align with the pipette tips of the liquid handling machine. Examples of such liquid handling machines include a Hamilton Microlab Star, Tecan EVO (150, 200) with Liquid Handling, a Beckman Coulter Biomek FX and NX) and a Perkin Elmer JANUS Automated Workstation.

For example, referring back to FIG. 1, apparatus 100 is configured to hold the cuvettes in twelve rows of eight which may align with a liquid handling machine having eight pipette tips. The apparatus also includes placement features configured to restrain movement of the plate within the liquid handling machine so that, for example, the liquid handling robot arm containing the pipette tips may align with the cuvettes inserted into the cuvette holders that are disposed on the plate. Placement features 160 identified in FIG. 100 include vertical support bars as well as horizontal skids or feet that include notches which may interface with features of the liquid handling machine in order to align the apparatus within the machine.

A Second Example Cuvette Holder

Figure 13:
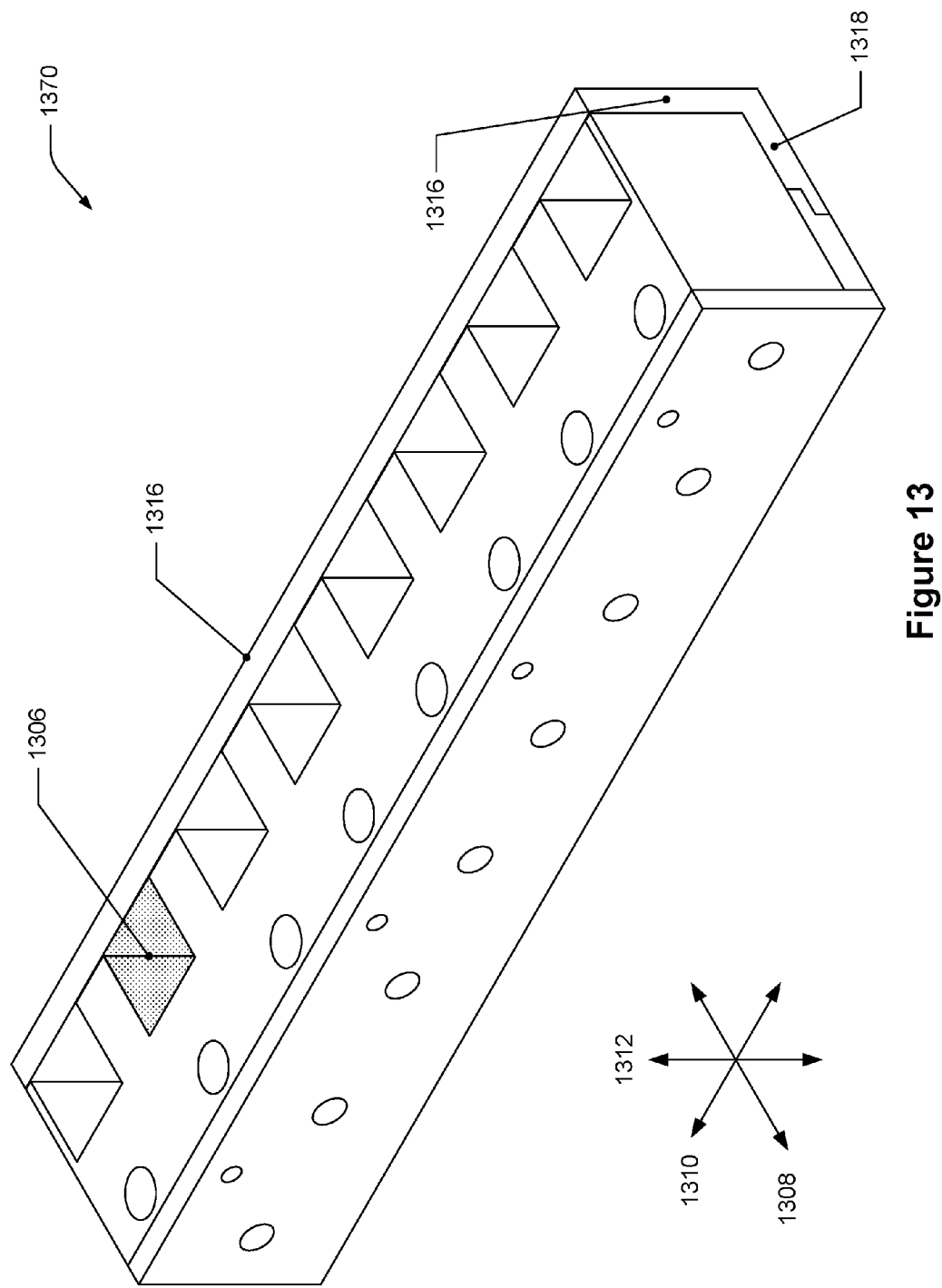
FIG. 13 depicts another example cuvette holder.

As mentioned above, the present disclosure includes another example embodiment of a cuvette holder (hereinafter "second cuvette holder") configured to perform electroporation of cuvettes that are inserted into the second example cuvette holder. FIG. 13 depicts another example cuvette holder that is configured to hold a plurality of cuvettes. The second cuvette holder 1370 may include some similar or identical features of cuvette holder 104; for instance, second cuvette holder 1370 includes a sidewall 1316, a bottom 1318, and a plurality of cuvette positioning features, such as an opening 1306 (only one of which is identified with shading) that may be configured similarly to such features in cuvette holder 104.

As discussed above, the plurality of cuvette positioning features, such as an opening 1306, of the second cuvette holder 1370 may be configured to secure a cuvette or restrain a movement of a cuvette that is inserted into the second cuvette holder 1370. For example, openings 1306 enable cuvettes to be inserted into an internal volume of the cuvette holder (discussed below), i.e. inserted vertically, but substantially restrain movement of the cuvette in an x-axis 1308 and a y-axis 1310. Additionally, opening 1306 may also prevent a cuvette from rotating about the z-axis 1312. Sidewall 1316 and bottom 1318 may also have a thermal conductivity of a metal or metal alloy, which may be greater than 150 W/(m K) such as about 205 W/(m K) for aluminum or about 385 W/(m K) for copper.

Figure 14:
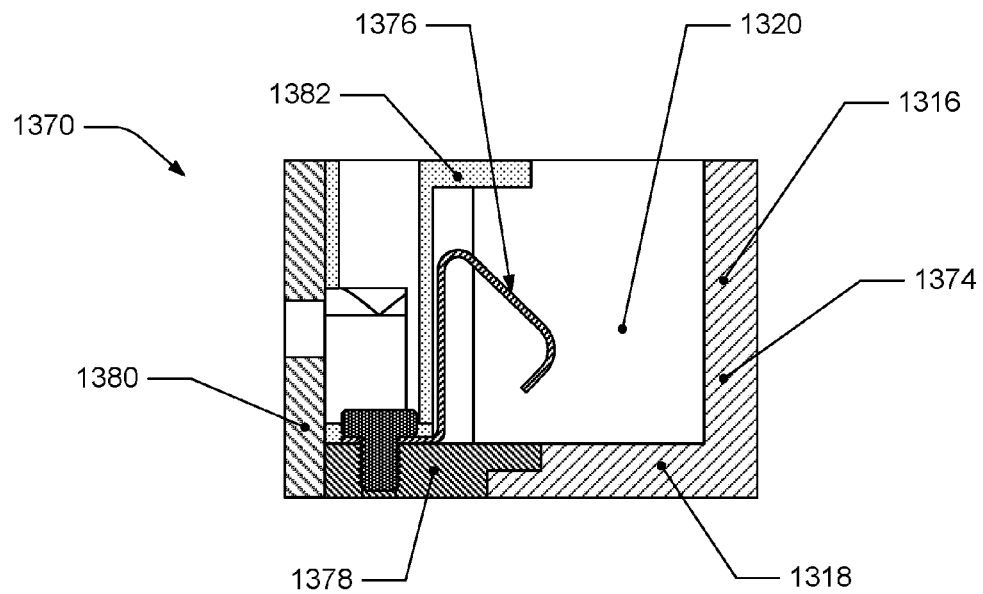
FIG. 14 depicts a cross-sectional view of the second cuvette holder of FIG. 13.

Similar to the above discussion, sidewall 1316 and bottom 1318 are in direct contact with each other and are therefore in thermal connection with each other as can be seen in FIG. 13 and FIG. 14 which depicts a cross-sectional view of the second cuvette holder of FIG. 13. In some embodiments, such as shown in FIGS. 13 and 14, sidewall 1316 and bottom 1318 may be portions of the same, continuous element. Sidewall 1316 and bottom 1318 also may at least partially define an internal volume 1320 of the second cuvette holder 1370 as shown in FIG. 14. Additionally, like discussed above, the cuvette positioning features, such as opening 1306, may also be configured to restrain a movement of a cuvette that is inserted into the internal volume 1320 such that a portion of each cuvette that is inserted into the internal volume 1320 is in thermal connection with sidewall 1316.

Figure 15:
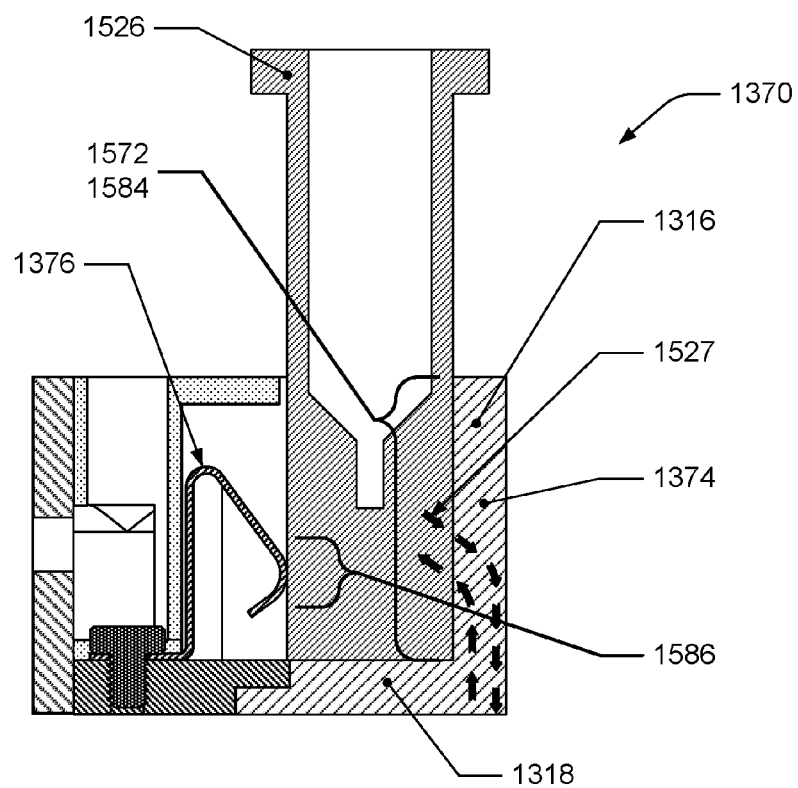
FIG. 15 depicts the cross-sectional view of the second cuvette holder of FIG. 14 with a cuvette inserted into the second cuvette holder.

FIG. 15 depicts the cross-sectional view of the second cuvette holder of FIG. 14 with a cuvette inserted into the second cuvette holder. Cuvette 1526 can be seen inserted into the internal volume 1320 of the second cuvette holder 1370. Similar to the above description with respect to FIG. 4, one or more of the cuvette positioning features, e.g., the opening 1306, has restrained movement of the cuvette 1526 in order to cause a portion 1572 of the cuvette 1526 to be in thermal connection, in direct physical contact, and/or in direct thermal contact with sidewall 1316. At least some of the cuvette 1526 may be thermally conductive, such as the electrodes referred to above. Such thermal connections between the cuvette, sidewall, and bottom create a thermal conduction pathway between all of these elements. Two exemplary thermal flows between the cuvette 1526, sidewall 1316, and bottom 1318 are identified with arrows as feature 1527.

Second cuvette holder 1370 includes a first electrode and a number N second electrodes that are electrically isolated from each other and from the first electrode. It should be noted that in some such configurations each second electrode is configured to be electrically coupled to the first electrode when a cuvette is inserted into the second cuvette holder such that an electrical pathway is created between the second electrode and the first electrode through the cuvette.

The second cuvette holder 1370 may be configured to hold a number N cuvettes, such as eight like depicted in FIG. 13, so that the number of second electrodes matches the number of cuvettes the second cuvette holder is configured to hold. Referring back to FIG. 14, a first electrode 1374 and a second electrode 1376 can be seen. Here, the sidewall 1316 is the first electrode 1374 and is therefore both an electrically conductive material and a thermally conductive material as described above. It should also be noted that in some embodiments, including as depicted in FIGS. 14 and 15, the sidewall 1316 and the bottom 1318 may be connected, or the same continuous piece, thereby also making the bottom 1318 the first electrode 1374. In some embodiments, the first electrode may be an item separate from the sidewall 1316, such as a wire or ribbon.

As noted above, the second cuvette holder 1370 may be configured such that the second electrodes 1376 are electrically isolated from each other and from the first electrode. Accordingly, the composition of the second cuvette holder 1370 includes both electrically conductive and non-electrically conductive material. For instance, as can be seen in FIG. 14, the second electrode 1376 is fastened to a first part 1378 of the second cuvette holder 1370 that is a non-electrically conductive material, such as a thermoplastic or a ceramic. The non-electrical conductivity of the first part 1378 enables it and the bottom 1318, e.g., the first electrode 1374, from being electrically coupled. Other parts of the second cuvette holder 1370, such as a second part 1380 and a third part 1382 identified in FIG. 14, may also be non-electrically conductive materials to maintain electrical isolation between all of the electrodes, except selectively electrically coupled when a cuvette is inserted into the second cuvette holder 1370.

This aforementioned electrical isolation between the all of the electrodes of the second cuvette holder 1370 enables the alternate, selective electrical coupling of one second electrode to the first electrode such that the current may travel between the one second electrode and the first electrode when a cuvette is inserted into the second cuvette holder; therefore, such configuration enables the alternative, sequential electroporation of each cuvette inserted into the second cuvette holder 1370.

Figure 16:
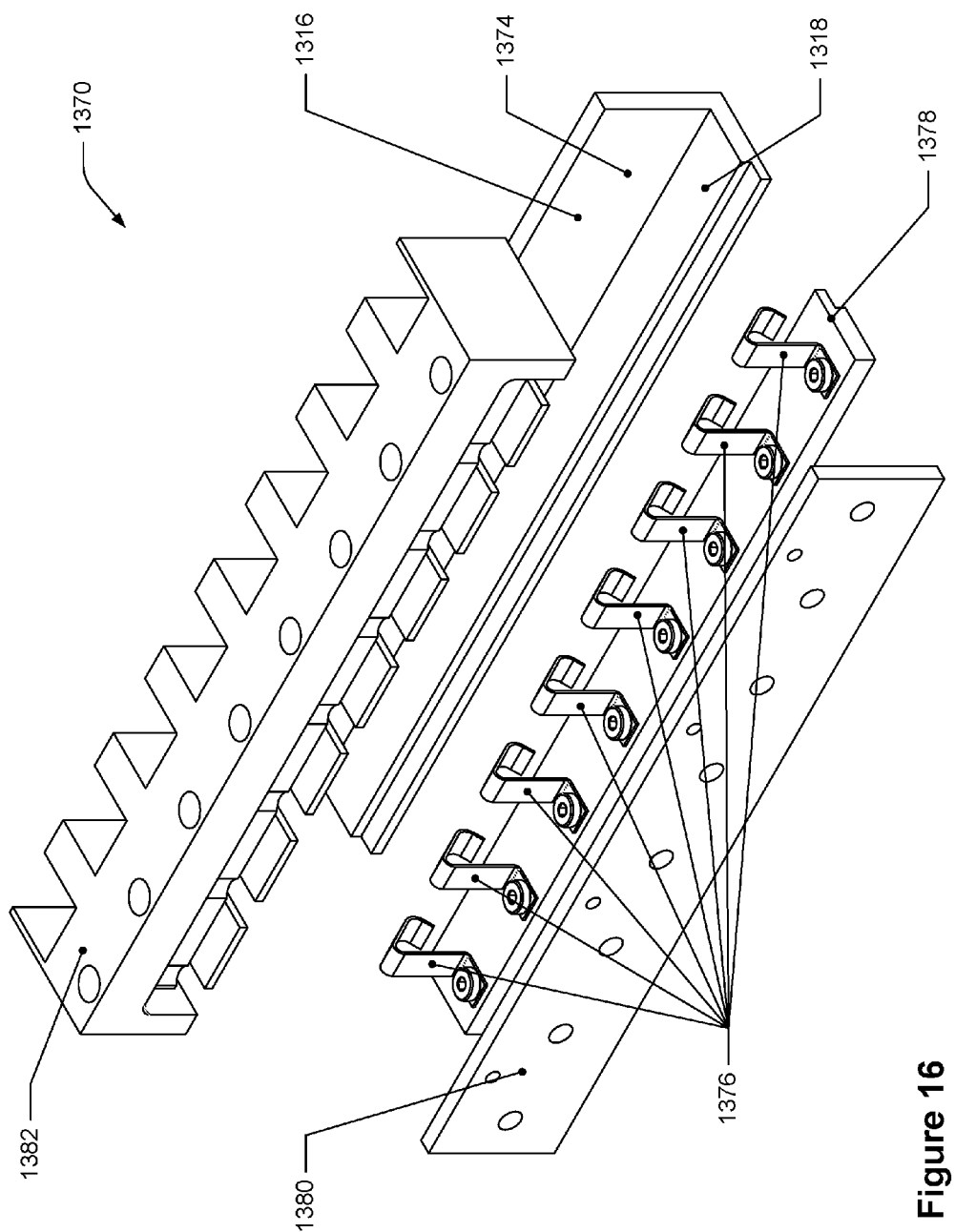
FIG. 16 depicts an exploded view of the second cuvette holder of FIG. 13.

The configuration and composition of the second cuvette may be further explained with FIG. 16 which depicts an exploded view of the second cuvette holder of FIG. 13. As can be seen, the second cuvette holder 1370 includes eight second electrodes 1376 which are connected to the non-electrically conductive first part 1378 while the first electrode 1374, e.g., sidewall 1316 and bottom 1318, are further electrically isolated due to the second part 1380 and the third part 1382 also being made of non-electrically conductive material.

Each cuvette positioning feature, e.g., opening 1306, of the second cuvette holder 1370 is also configured to restrain a movement of a cuvette that is inserted into the internal volume 1320 such that a third portion of each cuvette that is inserted into the internal volume is electrically coupled to the first electrode, and a fourth portion of each cuvette that is inserted into the internal volume is electrically coupled to one corresponding second electrode. For example, referring back to FIG. 15, the cuvette positioning feature, e.g., opening 1306 (not identified), has restrained a movement of cuvette 1526 (which has been inserted into the internal volume 1320 of the second cuvette holder 1370) to cause a third portion 1584 to be electrically coupled to the first electrode 1374. In some embodiments, like in FIG. 14, the third portion 1584 is also the portion 1372 that is in thermal connection with the sidewall 1316 and may be the electrode of the cuvette.

Figure 17:
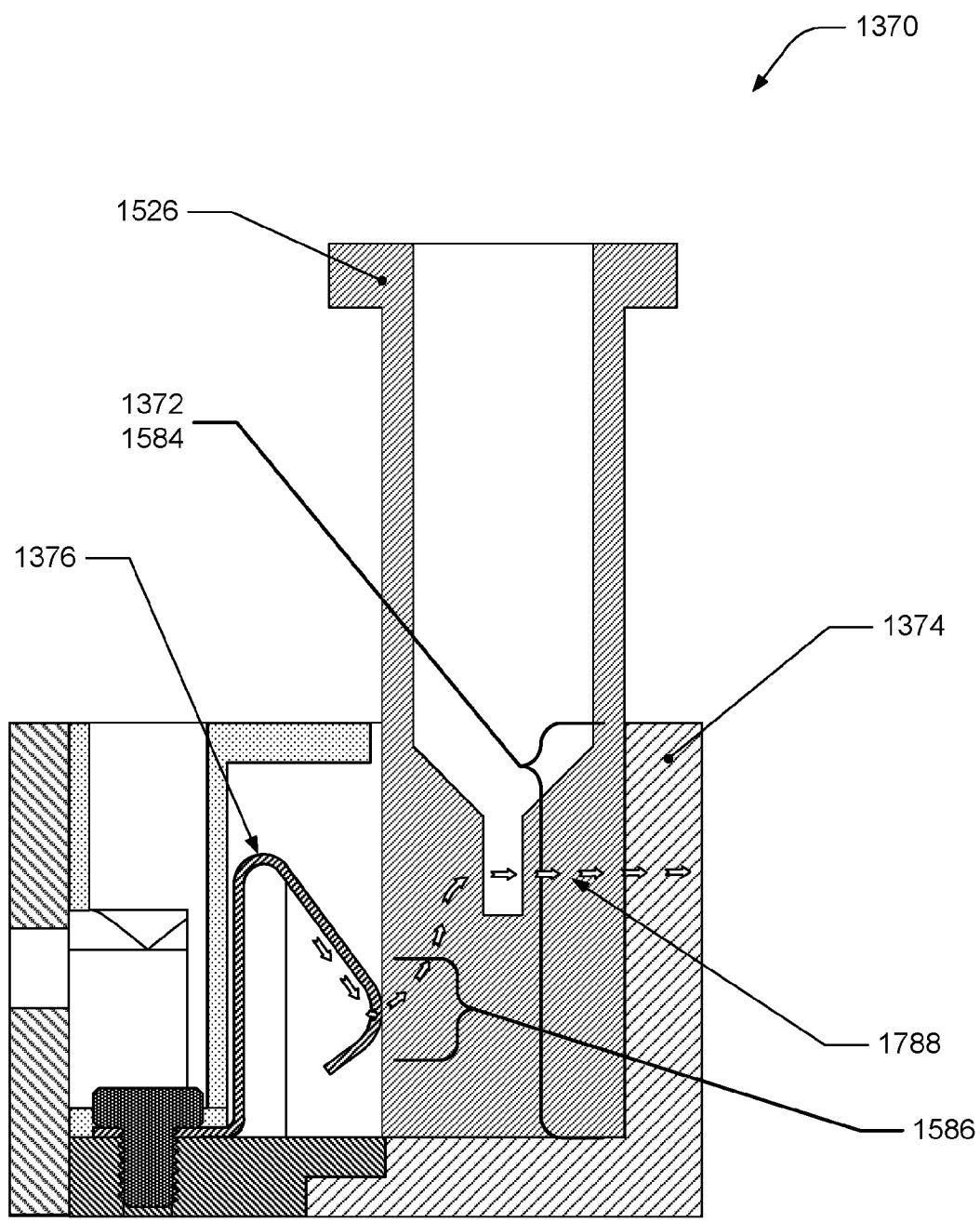
FIG. 17 depicts the cross-sectional view of the second cuvette holder of FIG. 15.

Additionally, the cuvette positioning feature, e.g., opening 1306 (not identified), has restrained a movement of cuvette 1526 to cause a fourth portion 1586 of the cuvette 1526 to be electrically coupled to the corresponding second electrode 1376. In some embodiments, the fourth portion 1586 may be the same element as the second portion discussed above as well as the other electrode of the cuvette. The electrical coupling between the first electrode 1374 and the third portion 1584, and between a second electrode 1376 and the fourth portion 1586, enables the selective electrical coupling to occur between the first electrode 1374 and the second electrode 1376 when an electrical current is electrically coupled to the second electrode 1376 and the first electrode is electrically coupled to a ground. For instance, FIG. 17 depicts the cross-sectional view of the second cuvette holder of FIG. 15. For illustrative purposes, FIG. 17 depicts an example, representational electrical flowpath 1788 from the second electrode 1376, through fourth portion 1586, through the cuvette 1526 (which may include through a solution within the cuvette), through the third portion 1584, and through the first electrode 1374 to the ground.

Switching Circuitry and Controllers

Figure 18:
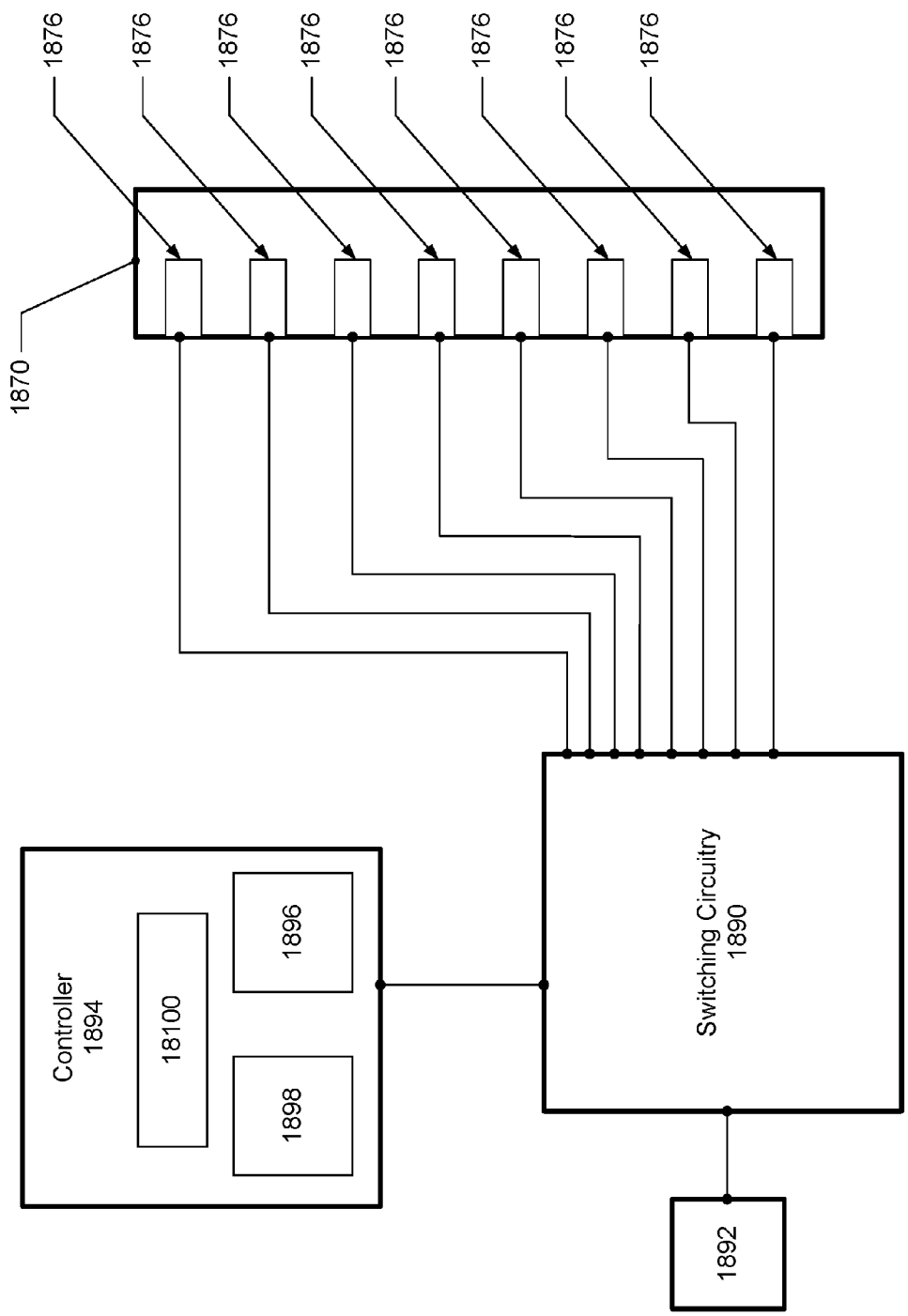
FIG. 18 depicts an example schematic of electrical coupling of the apparatus.

As stated above, the configuration of the second cuvette holder 1370 enables the alternative, sequential electroporation of each cuvette inserted into the second cuvette holder 1370. The apparatus may thus include switching circuitry configured to electrically couple one second electrode to a power supply while the other second electrodes are not electrically coupled to the power supply. FIG. 18 depicts an example schematic of the electrical coupling of the apparatus. As can be seen, switching circuitry 1890 is electrically coupled to each of the eight second electrodes 1876 of second cuvette holder 1870 and the switching circuitry is configured to alternatively, sequentially, and/or individually electrically couple power supply 1892 to each of the second electrodes 1876. The switching circuitry may include a power supply terminal (not identified) that is configured to receive a current from the power supply 1892. The switching circuitry may also use any known switch or switching method such as analog/mechanical switches and/or transistors (e.g., MOSFET transistors).

The apparatus may also include a controller configured to control the switching circuitry. FIG. 18 includes controller 1894 which may include one or more processors 18100 and a memory 1896 that may store control logic for causing the switching circuitry to alternatively electrically couple each second electrode 1876 to the power supply 1892 while the other second electrodes 1876 are not electrically coupled to the power supply 1892. The controller and switching circuitry may also be configured to adjust the current and the duration the current is delivered to each of the second electrodes such that the current and/or duration the current is delivered to one second electrode may differ from that delivered to another second electrode.

In some embodiments, the controller may also be configured to measure a resistance of a liquid or media located in a cuvette that is inserted into the second cuvette holder. This may be performed, for example, by applying a low voltage, such as a voltage below which electroporation occurs, and measuring the resistance of that applied low voltage across the solution in the cuvette. The controller may further be configured, as noted above, to adjust the current and/or duration the current is delivered to one second electrode based on the measurement of the resistance. This adjustment may be automatic or user controlled. The controller may also be configured to adjust the solution of the cuvette by, for example, causing the liquid handling machine to add, remove, or otherwise adjust the liquid or media in the cuvette.

The controller 1894 may be used to control one or more electroporation process conditions, including operations of a liquid handling machine. Controller 1894 may include one or more memory devices 1896, one or more mass storage devices 1898, and one or more processors 18100. Processor 18100 may include one or more CPUs, ASICs, general-purpose computer(s) and/or specific purpose computer(s), one or more analog and/or digital input/output connection (s), one or more stepper motor controller board(s), etc.

Controller 1894 may execute machine-readable system control instructions on processor 18100; the system control instructions, in some implementations, loaded into memory device 1896 from mass storage device 1898, and may include instructions for controlling the timing, volume, and mixture of cells and DNA inserted in one or more cuvettes in a cuvette holder, and other parameters of a particular electroporation process. System control instructions may be configured in any suitable way and may by implemented in software, in other implementations, the instructions may be implemented in hardware—for example, hard-coded as logic in an ASIC (application specific integrated circuit), or, in other implementations, implemented as a combination of software and hardware.

In some implementations, system control software may include input/output control instructions for controlling the various parameters described above. In some implementations, there may be a user interface associated with controller 1894. The user interface may include a display screen, graphical software displays of the apparatus and/or process conditions, and user input devices such as pointing devices, keyboards, touch screens, microphones, etc.

In some embodiments, the switching circuitry may be electrically coupled to each second electrode and to the power source, as shown in FIG. 18, but the controller may be electrically coupled directly to the power source. Additionally, the controller may be electrically coupled with, and configured to be in communication with, a computing device that may be electrically coupled with, and also configured to be in communication with, the liquid handling machine.

The apparatus may also be configured to apply electrical currents and voltages of varying ranges over particular times in order to generate electrical fields of different strengths. Some non-limiting examples include voltages ranging from about 0.20 kV to about 3 kV, 3000 V peak into greater than 3.3 kohm limited to 100 amp peak maximum, field strengths of about 12 kV/cm to about 25 kV/cm, and times from about 1.5 ms to about 4.0 ms.

Example Techniques for Electroporation

Figure 19:
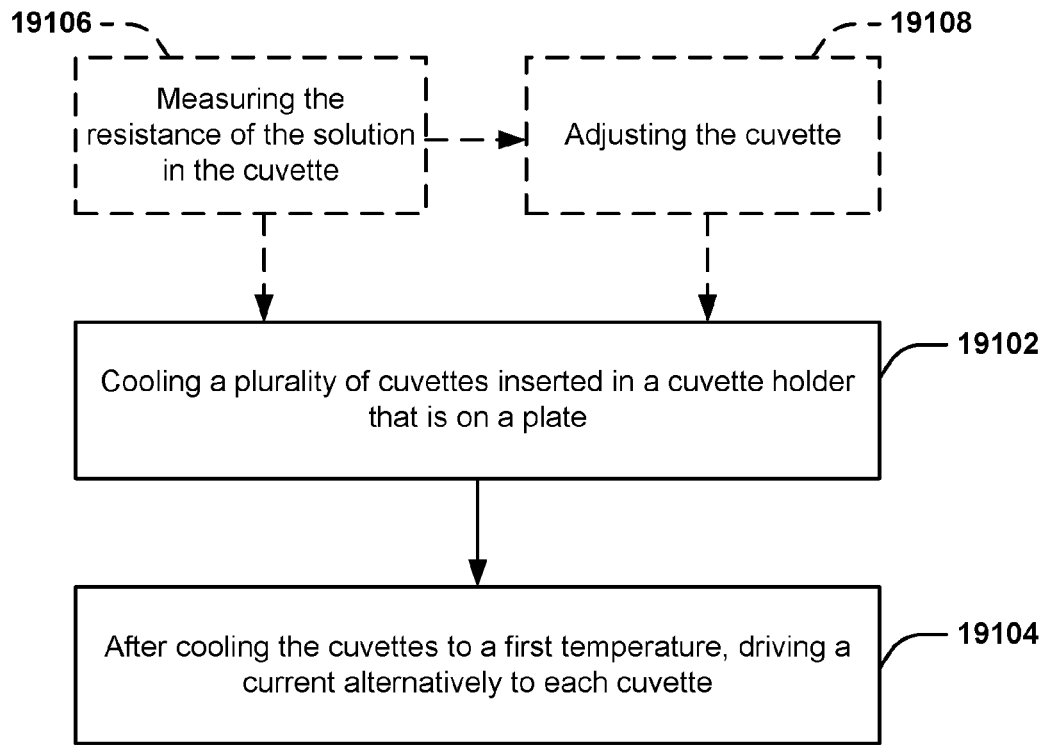
FIG. 19 depicts a flowchart of a first example technique for performing electroporation.

The present disclosure also includes techniques for using one or more of aspects of the apparatus disclosed herein to perform electroporation. FIG. 19 depicts a flowchart of a first example technique for performing electroporation. In block 19102, a plurality of cuvettes may be cooled, similar to described above. In some embodiments, each of the cuvettes may contain a solution and may be inserted into a cuvette holder that is disposed on the first surface of the plate. The bottom of the cuvette holder may be in a thermal connection with the first surface and with at least one sidewall of the cuvette holder such that heat may be conducted between the cuvette, the sidewall and the bottom of the cuvette holder, and the first surface of the plate. As described above, a fluid flowpath may be in thermal connection with the first surface, for instance the fluid flow path may be internal, at least in part, to the plate and the heat transfer fluid may be flowed (e.g., by a recirculating pump) through the fluid flowpath such that the first surface of the plate is cooled, thereby cooling the bottom and sidewall of the cuvette holder as well as the solution within the cuvette.

In block 19104, a current is driven alternately to each cuvette of the plurality of cuvettes as described above. The driven current may be configured to perform electroporation of the solution within each of the cuvettes. The current may not be applied to multiple cuvettes at one time, but rather may be alternately or sequentially applied to each one of the cuvettes. This current is also not driven to each cuvette until each cuvette is cooled to a first temperature, which may be the desired temperature to perform electroporation of the solution in each of the cuvettes.

In some embodiments, like described above, the current applied to each cuvette may flow through the second (and/or fourth) portion of the cuvette, through the solution of that cuvette, and through the portion (and/or third portion) of the cuvette to a ground. This application of the current may occur while the cuvette is in the internal volume of the cuvette holder (such as the second example cuvette holder) or while the cuvette is outside the cuvette holder, such as within a separate electroporation machine that may electroporate each cuvette. In the embodiments in which the current is applied while the cuvette is in the internal volume of the cuvette holder, such as the second example cuvette holder described above, the current may be driven alternately to the plurality of second electrodes on the cuvette holder, to a fourth portion of each cuvette electrically coupled to one second electrode, through the solution of that cuvette, and to the third portion of each cuvette electrically coupled to a first electrode that is electrically coupled to the ground.

In an optional block 19106, the resistance of the solution in one or more of the cuvettes may be measured before driving the current to the one or more cuvettes. This may provide feedback to a user about the solution, such as whether the salinity of the solution is too high or too low. In response to the measurement of block 19106, optional block 19108 may be also performed. This optional block 19108 may include adjusting, in response to the measurement and before driving the current to one of the cuvettes the solution in that cuvette, the current to be applied to that cuvette, and/or the duration the current that is to be applied to that cuvette. The cuvette may also be replaced with another cuvette.

In some electroporation processes, it may be advantageous to heat the electroporated solutions in the cuvettes. In some such embodiments, the cuvette holders may be removed from the plate after the electroporation described herein above and positioned on a second surface of a second plate in thermal connection with a second fluid flowpath. This second plate and second fluid flow path may be configured identically to the plate described hereinabove, but the heat transfer fluid flowed through the second fluid flowpath may be at a higher temperature than the plate used for cooling such that the temperature of the cuvettes in the cuvette holders on the second surface of the second plate is increased.

The controller described hereinabove may include control logic to perform some or all of the techniques described herein.

Example Experimental Results

The present disclosure has resulted in improvements to some electroporation processes. For instance, side-by-side experiments were performed between a manual electroporation method and a method using a liquid handling machine. The same plasmid construct, microbe type, electroporator, and electroporation cuvette were used for both methods. The manual method utilized ice or ice baths for most aspects of the process, such as cooling of the cells and DNA in separate containers and cooling the cuvettes containing the combined cells and DNA before and after electroporation. The apparatus was used during most aspects of the process using the liquid handling machine, such as cooling cuvettes containing cells, cuvettes containing DNA, and cuvettes containing the cells and DNA before and after electroporation. The time to execute a DNA transfer step, i.e., combining and mixing the cells and DNA and electroporating each cuvette, was reduced from about 90 minutes in the manual method to about 20 minutes in the method using the apparatus and the liquid handling machine. Additionally, although further experimentation and process refinement may be indicated, transfer efficiency was approximately the same between both methods.

What is claimed is:

1. An apparatus comprising:
a plurality of cuvette holders, wherein each cuvette holder is configured to hold a plurality of cuvettes and includes a bottom having a thermal conductivity greater than 150 W/(m K), a sidewall having a thermal conductivity greater than 150 W/(m K), a plurality of cuvette positioning features, a first electrode, and a plurality of second electrodes that are electrically isolated from each other and from the first electrode, wherein:
the sidewall and the bottom are in thermal connection with each other and at least partially define an internal volume of the cuvette holder,
each cuvette positioning feature is configured to restrain a movement of a cuvette that is inserted into the internal volume such that a portion of each cuvette that is inserted into the internal volume is in thermal connection with the sidewall,
the first electrode and the plurality of second electrodes are configured such that insertion of a cuvette into the internal volume causes the cuvette to be electrically coupled to the first electrode and to one of the plurality of second electrodes; and
a plate having a thermal conductivity greater than 150 W/(m K) and including a first surface and a plurality alignment features, wherein:
each alignment feature is configured to restrain a movement of a cuvette holder that is positioned on the first surface with respect to the first surface, and
the bottom of each cuvette holder that is placed on the first surface and restrained by at least one alignment feature is in thermal connection with the first surface; and a fluid flowpath in thermal connection with the first surface.

2. The apparatus of claim 1, wherein:
each cuvette holder further includes a second sidewall having a thermal conductivity greater than 150 W/(m K),
the second sidewall is in thermal connection with the bottom, and
each cuvette positioning feature is further configured to restrain a movement of a cuvette that is inserted into the internal volume such that a second portion of each cuvette that is inserted into the internal volume is in thermal connection with the second sidewall.

3. The apparatus of claim 1, wherein each cuvette holder includes a mounting feature configured to interface with an alignment feature of the plurality of alignment features to restrain a movement of the cuvette holder.

4. The apparatus of claim 1, wherein each cuvette holder is configured to hold exactly eight cuvettes.

5. The apparatus of claim 1, wherein the plate is configured to accommodate twelve cuvette holders on the first surface.

6. The apparatus of claim 1, wherein each cuvette positioning feature is configured to restrain a movement of a cuvette that is inserted into the internal volume such that the portion of each cuvette that is inserted into the internal volume is in direct thermal contact with the sidewall.

7. The apparatus of claim 1, wherein a surface of the fluid flowpath is defined, at least in part, by the plate.

8. The apparatus of claim 7, wherein a surface of the fluid flowpath is further defined, at least in part, by a cover over a second surface of the plate.

9. The apparatus of claim 1, wherein the fluid flowpath follows a serpentine path.

10. The apparatus of claim 1, wherein the fluid flowpath is configured to cause at least a section of the first surface on which the cuvette holders are disposed to have a substantially uniform temperature when a heat transfer fluid flows through the fluid flowpath.

11. The apparatus of claim 10, wherein a heat transfer fluid flows through the fluid flowpath and causes at least the section of the first surface to have a substantially uniform temperature.

12. The apparatus of claim 1, further comprising a pump, wherein the pump is configured to flow the heat transfer fluid through the fluid flowpath.

13. The apparatus of claim 1, wherein:
the cuvette holder is configured to hold N cuvettes and the plurality of second electrodes includes N second electrodes, and
each cuvette positioning feature is further configured to restrain a movement of a cuvette that is inserted into the internal volume such that:
a third portion of each cuvette that is inserted into the internal volume is electrically coupled to the first electrode, and
a fourth portion of each cuvette that is inserted into the internal volume is electrically coupled to one corresponding Nth second electrode.

14. The apparatus of claim 13, wherein the sidewall is electrically conductive and is the first electrode.

15. The apparatus of claim 13, wherein:
the third portion of each cuvette inserted into the internal volume is the portion of that cuvette, and
the fourth portion of each cuvette inserted into the internal volume is in thermal connection with the second sidewall.

16. The apparatus of claim 1, further comprising switching circuitry, wherein:
each second electrode is electrically coupled with the switching circuitry, and
the switching circuitry is configured to electrically couple one second electrode to a power supply while the other second electrodes are not electrically coupled to the power supply.

17. The apparatus of claim 16, further comprising a controller configured to control the switching circuitry, wherein the controller includes control logic for:
causing the switching circuitry to alternatively electrically couple each second electrode to the power supply while the other second electrodes are not electrically coupled to the power supply.

18. The apparatus of claim 17, wherein the controller further includes control logic for:
measuring the resistance of a solution in a cuvette that has been inserted into the internal volume.

19. The apparatus of claim 18, wherein the controller further includes control logic for:
adjusting, based on the measurement of the resistance of the solution in the cuvette that has been inserted into the internal volume, one or more of the following: the solution in that cuvette, the current to be applied to that cuvette, and the duration the current is to be applied to that cuvette.

20. The apparatus of claim 1, further comprising a plurality of cuvettes, wherein:
each cuvette is inserted in the internal volume of the cuvette holder,
a movement of each cuvette is restrained by a corresponding cuvette positioning feature, and
each cuvette is electrically coupled to the first electrode and to one of the plurality of second electrodes.

21. The apparatus of claim 1, further comprising a plurality of cuvettes, wherein:
each cuvette is inserted in the internal volume of the cuvette holder,
a movement of each cuvette is restrained by a corresponding cuvette positioning feature, and
a portion of each cuvette is in thermal connection with the sidewall.

22. The apparatus of claim 1, wherein the apparatus is configured to place 96 cuvettes in thermal connection with the first surface of the plate at one time.

23. An apparatus comprising:
a plurality of cuvette holders, wherein each cuvette holder is configured to hold a plurality of cuvettes and includes a bottom and a sidewall that are in thermal connection with each other and at least partially define an internal volume of the cuvette holder, a first electrode, and a plurality of second electrodes that are electrically isolated from each other and from the first electrode;
a plate including a first surface; and
a fluid flowpath in thermal connection with the first surface, wherein:
the first electrode and the plurality of second electrodes are configured such that insertion of a cuvette into the internal volume causes a portion the cuvette to be in thermal connection with the sidewall and causes the cuvette to be electrically coupled to the first electrode and to one of the plurality of second electrodes, and
the bottom of each cuvette holder that is placed on the first surface is in thermal connection with the first surface.

24. The apparatus of claim 23, wherein:
the cuvette holder is further configured to hold N cuvettes
the cuvette holder further includes N second electrodes, and
the first electrode and the plurality of second electrodes are further configured such that insertion of each cuvette into the internal volume causes each cuvette to be electrically coupled to one corresponding Nth second electrode.

* * * * *